(12) United States Patent
Wang

(10) Patent No.: US 10,584,523 B2
(45) Date of Patent: Mar. 10, 2020

(54) HINGED COMPONENT MADE FROM HIGH DENSITY UNIMODAL POLYETHYLENE

(71) Applicant: NOVA Chemicals (International) S.A., Fribourg (CH)

(72) Inventor: XiaoChuan Wang, Calgary (CA)

(73) Assignee: NOVA Chemicals (International) S.A., Fribourg (CH)

( * ) Notice: Subject to any disclaimer, the term of this patent is extended or adjusted under 35 U.S.C. 154(b) by 0 days.

(21) Appl. No.: 15/622,101

(22) Filed: Jun. 14, 2017

(65) Prior Publication Data

US 2017/0370135 A1    Dec. 28, 2017

(30) Foreign Application Priority Data

Jun. 22, 2016 (CA) .................................. 2933778

(51) Int. Cl.

| | |
|---|---|
| *C08F 10/02* | (2006.01) |
| *G01N 3/56* | (2006.01) |
| *E05D 1/02* | (2006.01) |
| *B65D 47/00* | (2006.01) |
| *G01N 3/00* | (2006.01) |
| *G01N 3/20* | (2006.01) |
| *G01N 3/32* | (2006.01) |
| *C08F 210/02* | (2006.01) |
| *C08F 110/02* | (2006.01) |

(52) U.S. Cl.
CPC ............... *E05D 1/02* (2013.01); *C08F 10/02* (2013.01); *B65D 47/00* (2013.01); *C08F 110/02* (2013.01); *C08F 210/02* (2013.01); *G01N 3/00* (2013.01); *G01N 3/20* (2013.01); *G01N 3/32* (2013.01); *G01N 3/56* (2013.01)

(58) Field of Classification Search
None
See application file for complete search history.

(56) References Cited

U.S. PATENT DOCUMENTS

| | | | |
|---|---|---|---|
| 4,688,675 A | * | 8/1987 | Miller .................. B65D 21/064 206/508 |
| 5,292,845 A | | 3/1994 | Kawasaki et al. |
| 5,342,868 A | | 8/1994 | Kimura et al. |
| 5,376,439 A | | 12/1994 | Hodgson et al. |
| 5,863,655 A | * | 1/1999 | Mock .................. B29C 45/0081 215/235 |

(Continued)

FOREIGN PATENT DOCUMENTS

| | | | |
|---|---|---|---|
| WO | 93/03093 A1 | 2/1993 | |
| WO | WO-9748613 A1 | * 12/1997 | ........... B65D 43/162 |

(Continued)

OTHER PUBLICATIONS

NOVA Chemicals, SCLAIR 2807 product data sheet. Aug. 22, 2013 (Year: 2013).*

(Continued)

*Primary Examiner* — Richard A Huhn
(74) *Attorney, Agent, or Firm* — Julie L. Heinrich

(57) ABSTRACT

A hinged component comprises a polyethylene composition having a density of from 0.940 to 0.965 g/cm³, a melt index of less than 30 g/10 min, a molecular weight distribution $M_w/M_n$ of less than 5.0 and a unimodal profile in a gel permeation chromatograph.

26 Claims, 10 Drawing Sheets

(a) = 0.58 mm,
(b) = 0.75 mm,
(c) = 0.18 mm.

(56) References Cited

U.S. PATENT DOCUMENTS

| | | | |
|---|---|---|---|
| 5,981,636 | A | 11/1999 | Amos et al. |
| 6,465,551 | B1 | 10/2002 | Zhao et al. |
| 6,599,971 | B2 | 7/2003 | Dotson et al. |
| 8,039,569 | B2 | 10/2011 | Kipke et al. |
| 9,273,199 | B2 | 3/2016 | Domoy et al. |
| 2013/0085244 | A1 | 4/2013 | Zhao et al. |
| 2013/0343808 | A1 | 12/2013 | Domoy et al. |
| 2014/0275426 | A1 | 9/2014 | Rycroft et al. |

FOREIGN PATENT DOCUMENTS

| | | | |
|---|---|---|---|
| WO | 2005/121239 | A2 | 12/2005 |
| WO | 2011/050042 | A1 | 4/2011 |
| WO | 2015/042561 | A1 | 3/2015 |
| WO | 2015/042562 | A1 | 3/2015 |
| WO | 2015/042563 | A1 | 3/2015 |

OTHER PUBLICATIONS

MatWeb webpage for NOVA Chemicals SCLAIR 2908. Archived by the Internet Archive Wayback Machine on Sep. 30, 2015. Retrieved on Dec. 27, 2017. (Year: 2015).*

Randall, James C.; A Review of High Resolution Liquid 13Carbon Nuclear Magnetic Resonance Characterizations of Ethylene-Based Polymers; JMS-Rev. Macromol. Chem. Phys., (1989); C29(2 & 3), pp. 201-202 and 285-286.

ASTM D3124-98 (Reapproved 2011); Standard Test Method for Vinylidene Unsaturation in Polyethylene by Infrared Spectrophotometry; Copyright ASTM International; Current edition approved Feb. 1, 2011. Published Mar. 2011. Originally approved in 1972. Last previous edition approved in 2003 as D3124-98(2003). pp. 1-4.

ASTM D6474-99 (Reapproved 2006); Standard Test Method for Determining Molecular Weight Distribution and Molecular Weight Averages of Polyolefins by High Temperature Gel Permeation Chromatography; Copyright ASTM International; Current edition approved Mar. 15, 2006. Published Apr. 2006. Originally approved in 1999. Last previous edition approved in 1999 as D6474-99. pp. 1-6.

ASTM D6645-01 (Reapproved 2010); Standard Test Method for Methyl (Comonomer) Content in Polyethylene by Infrared Spectrophotometry; Copyright ASTM International; Current edition approved Jan. 1, 2010. Published Jan. 2010. Originally approved in 2001. Last previous edition approved in 2001 as D6645-01. pp. 1-4.

ASTM D 1238-04; Standard Test Method for Melt Flow Rates of Thermoplastics by Extrusion Plastometer; Copyright ASTM International; Current edition approved Mar. 1, 2004. Published Apr. 2004. Originally approved in 1965. Last previous edition approved in 2001 as D 1238-01. pp. 1-13.

ASTM D1525-09; Standard Test Method for Vicat Softening Temperature of Plastics; Copyright ASTM International; Current edition approved Nov. 15, 2009. Published Dec. 2009. Originally approved in 1958. Last previous edition approved in 2007 as D1525-07. pp. 1-10.

ASTM D256-10; Standard Test Methods for Determining the Izod Pendulum Impact Resistance of Plastics; Copyright ASTM International; Current edition approved May 1, 2010. Published Jun. 2010. Originally approved in 1926. Last previous edition approved in 2006 as D256-06a. pp. 1-20.

ASTM D792-13; Standard Test Methods for Density and Specific Gravity (Relative Density) of plastics by Displacement; Copyright ASTM International; Current edition approved Nov. 1, 2013. Published Nov. 2013. Originally approved in 1944. Last previous edition approved in 2008 as D792-08. pp. 1-6.

ASTM D5227-13; Standard Test Method for Measurement of Hexane Extractable Content of Polyolefins; Copyright ASTM International; Current edition approved Jun. 1, 2013. Published Jul. 2013. Originally approved in 1992. Last previous edition approved in 2008 as D5227-01 (2008). pp. 1-4.

ASTM D638-14; Standard Test Method for Tensile Properties of Plastics; Copyright ASTM International; Current edition approved Dec. 15, 2014. Published Mar. 2015. Originally approved in 1941. Last previous edition approved in 2010 as D638-10. pp. 1-17.

ASTM D790-15; Standard Test Methods for Flexural Properties of Unreinforced and Reinforced Plastics and Electrical Insulating Materials; Copyright ASTM International; Current edition approved Dec. 1, 2015. Published Jan. 2016. Originally approved in 1970. Last previous edition approved in 2010 as D790-10. pp. 1-12.

ASTM D1693-15; Standard Test Method for Environmental Stress-Cracking of Ethylene Plastics; Copyright ASTM International; Current edition approved May 1, 2015. Published Jun. 2015. Originally approved in 1959. Last previous edition approved in 2013 as D1693-13. pp. 1-11.

ASTM D648-16; Standard Test Method for Deflection Temperature of Plastics Under Flexural Load in the Edgewise Position; Copyright ASTM International; Current edition approved Apr. 1, 2016. Published Apr. 2016. Originally approved in 1941. Last previous edition approved in 2007 as D648-07, which was withdrawn Jan. 2016 and reinstated in Apr. 2016. pp. 1-14.

* cited by examiner

HINGED COMPONENT MADE FROM HIGH DENSITY UNIMODAL POLYETHYLENE

The present disclosure is directed to hinged components made from polyethylene homopolymers or copolymers. The polyethylene compositions have a relatively narrow molecular weight distribution (e.g., a $M_w/M_n$ of less than about 5.0), a density in the range of from about 0.940 to about 0.965 g/cm$^3$, and a melt index $I_2$ of below about 30 g/10 min. The hinged components may be present in, for example, a flip top cap or closure which can be used to seal a bottle, container or the like.

Hinged components such as hinged closures for bottles have traditionally been made with polypropylene (PP) due to the fact the polypropylene imparts high levels of durability to the hinge structure. However, since the economic climate does not always favor the use of PP in closure applications, other polymers, such as high density polyethylene have been explored as replacement materials.

U.S. Patent Application Publication No. 2014/0275426 discloses a polymer blend comprising a linear low density polyethylene copolymer and a high density polyethylene homopolymer. The blend performed well in polymer bent strip testing.

U.S. Pat. No. 9,273,199 and U.S. Patent Application Publication No. 2013/0343808 disclose that a blend comprising two high density polyethylene components can be injection molded into hinged closures having hinge performance which is comparable to that of hinges made from polypropylene.

We now report that hinged components made from simple, unblended polyethylene compositions also have useful levels of performance. Hence, the present disclosure provides economical resin solutions for application in hinged components (such as, caps and closures) while still maintaining acceptable levels of performance.

An embodiment of the disclosure is a hinged component comprising a polyethylene composition which is not a polymer blend and has a density of from 0.940 to 0.965 g/cm$^3$, a melt index, $I_2$ of less than 30 g/10 min, a molecular weight distribution, $M_w/M_n$ of less than 5.0, and a unimodal profile in a GPC chromatograph.

In an embodiment of the disclosure, a hinged component comprises a polyethylene composition having a melt flow ratio, $I_{21}/I_2$ of less than 40.

In an embodiment of the disclosure, a hinged component comprises a polyethylene composition having a molecular weight distribution, $M_w/M_n$ of less than 3.5.

In an embodiment of the disclosure, a hinged component comprises a polyethylene composition having a density of from 0.949 to 0.963 g/cm$^3$.

In an embodiment of the disclosure, a hinged component has an average hinge life of at least 2,500 cycles.

In an embodiment of the disclosure, a hinged component has an average hinge life of at least 3,500 cycles.

In an embodiment of the disclosure, a hinged component comprises a polyethylene composition having fewer than 0.8 parts per million of titanium.

In an embodiment of the disclosure, a hinged component comprises a polyethylene composition comprising polymerized ethylene and 1-butene.

In an embodiment of the disclosure, a hinged component is injection molded.

In an embodiment of the disclosure, a hinged component comprises a polyethylene composition having a melt index, $I_2$ of less than 10 g/10 min.

In an embodiment of the disclosure, a hinged component comprises a polyethylene composition having a melt index, $I_2$ of at least 10 g/10 min.

In an embodiment of the disclosure, a hinged component comprises a polyethylene composition which is a polyethylene copolymer of ethylene and one or more than one alpha-olefin.

In an embodiment of the disclosure, a hinged component comprises a polyethylene composition which is an ethylene homopolymer.

In an embodiment of the disclosure, a hinged component comprises a polyethylene composition having a Mz of less than 450,000.

In an embodiment of the disclosure, a hinged component comprises a polyethylene composition having a Mz/Mw of less than 3.0

In an embodiment of the disclosure, a hinged component comprises a polyethylene composition having a melt index, $I_2$ of less than 20 g/10 min.

In an embodiment of the disclosure, a hinged component comprises a polyethylene composition having a melt flow ratio, $I_{21}/I_2$ of less than 30.

In an embodiment of the disclosure, a hinged component comprises a polyethylene composition having an amount of terminal unsaturation of at least 0.45 per 1000 carbon atoms.

In an embodiment of the disclosure, a hinged component comprises a polyethylene composition having a total amount of unsaturation of at least 0.50 per 1000 carbon atoms.

In an embodiment of the disclosure, a hinged component comprises a polyethylene composition having a melt index, $I_2$ of from 2.5 to 9.5 g/10 min.

In an embodiment of the disclosure, a hinged component comprises a polyethylene composition having a melt index, $I_2$ of from 10.0 to 19.5 g/10 min.

In an embodiment of the disclosure, a hinged component is a closure.

In an embodiment of the disclosure, a hinged component comprises a polyethylene composition made in a solution phase polymerization reactor.

In an embodiment of the disclosure, a hinged component comprises a polyethylene composition made with a Ziegler-Natta catalyst.

BRIEF DESCRIPTION OF THE DRAWINGS

FIGS. 1 through 5 show gel permeation chromatographs for the unimodal polyethylene compositions used in Examples 1 through 5 respectively.

THE POLYETHYLENE COMPOSITION

Figure 1:
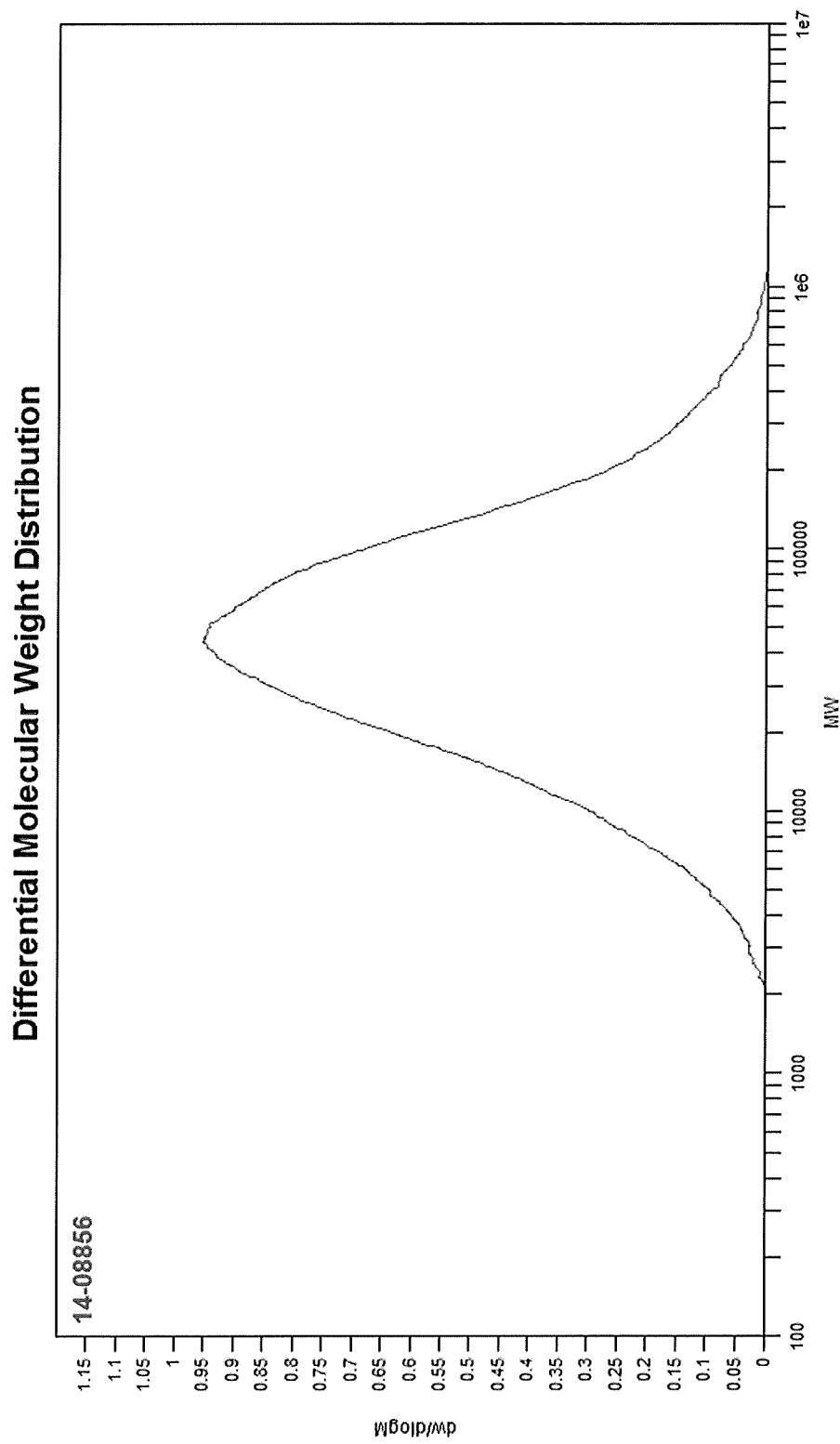
FIGS. 1-5.

In an embodiment of the present disclosure, the polymer composition is not a polymer blend. The phrase "polymer blend" as used in the present disclosure means a polyethylene composition which is comprised of at least two major different polymer composition components (by "major" it is meant that each of the different polymers comprise at least 5 or more weight percent of the total weight of the polymer blend). That is, in an embodiment of the disclosure, the polyethylene compositions are neither the result of in situ reactor blending of different polymers (including those made with multiple catalysts and/or different reactors operating under different conditions) nor dry blending or melt blending methods.

In an embodiment of the present disclosure, the polyethylene composition has a density from 0.940 to 0.967 g/cm$^3$. In further embodiments of the present disclosure, the polyethylene composition has a density of from 0.940 to 0.965 g/cm$^3$, or from 0.949 to 0.963 g/cm$^3$.

In an embodiment of the disclosure, the polyethylene composition has a melt index, $I_2$ as determined according to ASTM D1238 (2.16 kg/190° C.) of less than about 30 g/10 min. In further embodiments of the disclosure, the polyethylene composition has a melt index, $I_2$ as determined according to ASTM D1238 (2.16 kg/190° C.) of less than about 28 g/10 min, or less than about 26 g/10 min, or less than about 24 g/10 min, or less than about 22 g/10 min, or less than about 20 g/10 min, or less than about 18 g/10 min, or less than about 15 g/10 min, or less than about 10 g/10 min.

In an embodiment of the disclosure, the polyethylene composition has a melt index, $I_2$ as determined according to ASTM D1238 (2.16 kg/190° C.) of from 0.5 to less than 10.0 g/10 min. In further embodiments of the disclosure, the polyethylene composition has a melt index, $I_2$ as determined according to ASTM D1238 (2.16 kg/190° C.) of from 0.5 to 9.5 g/10 min, or from 1.0 to 9.0 g/10 min, or from 2.5 to 7.5 g/10 min, or from 2.0 to 9.5 g/10 min, or from 2.5 to 9.5 g/10 min.

In an embodiment of the disclosure, the polyethylene composition has a melt index, $I_2$ as determined according to ASTM D1238 (2.16 kg/190° C.) of at least 10.0 g/10 min.

In an embodiment of the disclosure, the polyethylene composition has a melt index, $I_2$ as determined according to ASTM D1238 (2.16 kg/190° C.) of from 10.0 to 30.0 g/10 min. In further embodiments of the disclosure, the polyethylene composition has a melt index, $I_2$ as determined according to ASTM D1238 (2.16 kg/190° C.) of from greater than 10.0 to 28.0 g/10 min, or from greater than 10.0 to 26.0 g/10 min, or from greater than 10.0 to 24.0 g/10 min, or from greater than 10.0 to 22.0 g/10 min, or from greater than 10.0 to 20.0 g/10 min, or from greater than 10.0 to 19.5 g/10 min, or from 10.0 to 28.0 g/10 min, or from 10.0 to 26.0 g/10 min, or from 10.0 to 24.0 g/10 min, or from 10.0 to 22.0 g/10 min, or from 10.0 to 20.0 g/10 min, or from 10.0 to 19.5 g/10 min.

In an embodiment of the disclosure, the polyethylene composition has a melt flow ratio (MFR) defined by $I_{21}/I_2$ of less than about 40. In further embodiments of the disclosure, the polyethylene composition has a melt flow ratio, $I_{21}/I_2$ of less than about 30, or from about 15 to about 30, or from about 20 to about 30.

In an embodiment of the present disclosure, the polyethylene composition has a unimodal profile in a gel permeation chromatograph obtained according to the method of ASTM D6474-99. The term "unimodal" is herein defined to mean there will be only one significant peak or maximum evident in the GPC-curve. A unimodal profile includes a broad unimodal profile. Alternatively, the term "unimodal" connotes the presence of a single maxima in a molecular weight distribution curve generated according to the method of ASTM D6474-99. In contrast, by the term "bimodal", it is meant that there will be a secondary peak or shoulder evident in a GPC-curve which represents a higher or lower molecular weight component (i.e., the molecular weight distribution, can be said to have two maxima in a molecular weight distribution curve). Alternatively, the term "bimodal" connotes the presence of two maxima including peaks and/or shoulders in a molecular weight distribution curve generated according to the method of ASTM D6474-99. The term "multi-modal" denotes the presence of two or more maxima including peaks and/or shoulders in a molecular weight distribution curve generated according to the method of ASTM D6474-99.

In an embodiment of the present disclosure, the polyethylene composition has an ESCR Condition B (10% IGEPAL) of at least 1 hour.

In an embodiment of the present disclosure, the polyethylene composition has an ESCR Condition B (10% IGEPAL) of from 1 to 10 hours.

In an embodiment of the disclosure, the polyethylene composition has a weight average molecular weight (Mw) from about 20,000 to about 100,000. In other embodiments of the disclosure, the unimodal polyethylene composition has a weight average molecular weight (Mw) from about 25,000, to about 85,000, or from about 30,000 to about 85,000, or from about 35,000 to about 80,000, or from about 40,000 to about 80,000, or from about 40,000 to about 75,000, or from about 45,000 to about 80,000, or from 50,000 to 75,000, or from 55,000 to 75,000.

In an embodiment of the disclosure, the polyethylene composition has a molecular weight distribution ($M_w/M_n$) of less than about 5.0. In further embodiments of the disclosure, the polyethylene composition has a molecular weight distribution ($M_w/M_n$) of less than about 4.5, or less than about 4.0, or less than about 3.5, or less than about 3.0, or from about 2.0 to about 5.0, or from about 2.0 to about 4.5, or from about 2.0 to about 4.0, or from about 2.0 to about 3.5, or from about 2.5 to about 4.0, or from about 2.5 to about 3.5.

In an embodiment of the disclosure, the polyethylene composition has a z-average molecular weight (Mz) from about 75,000 to about 450,000. In other embodiments of the disclosure, the unimodal polyethylene composition has a weight average molecular weight ($M_z$) from about 100,000, to about 400,000, or from about 100,000 to about 350,000, or from about 75,000 to about 300,000, or from about 75,000 to about 250,000, or from about 100,000 to about 250,000, or from about 75,000 to about 225,000, or from about 75,000 to about 200,000, or from about 100,000 to about 225,000, or less than about 450,000, or less than about 400,000, or less than about 350,000, or less than about 300,000, or less than about 250,000, or less than about 200,000.

In an embodiment of the disclosure, the polyethylene composition has a Z-average molecular weight distribution ($M_z/M_w$) of less than about 4.5. In further embodiments of the disclosure, the polyethylene composition has a z-average molecular weight distribution ($M_z/M_w$) of less than about 4.0, or less than about 3.5, or less than about 3.0, or from about 2.0 to about 4.5, or from about 2.5 to about 4.0, or from about 2.0 to about 3.5.

In an embodiment of the disclosure, the polyethylene composition has an amount of terminal unsaturation of at least 0.35 per 1000 carbons (or per 1000 carbon atoms), or at least 0.40 per 1000 carbons, or at least 0.45 per 1000 carbons, or greater than 0.45 per 1000 carbons, or at least 0.50 per 1000 carbons, or greater than 0.50 per 1000 carbons, or at least 0.55 per 1000 carbons, or greater than 0.55 per 1000 carbons, or at least 0.60 per 1000 carbons, or greater than 0.60 per 1000 carbons, or at least 0.65 per 1000 carbons, or greater than 0.65 per 1000 carbons, or at least 0.70 per 1000 carbons, or greater than 0.70 per 1000 carbons.

In an embodiment of the disclosure, the polyethylene composition has a total amount of unsaturation (which includes internal, side chain, and terminal unsaturation) of at least 0.40 per 1000 carbons (or per 1000 carbon atoms), or at least 0.45 per 1000 carbons, or at least 0.50 per 1000 carbons, or greater than 0.50 per 1000 carbons, or at least 0.55 per 1000 carbons, or greater than 0.55 per 1000 carbons, or at least 0.60 per 1000 carbons, or greater than 0.60 per thousand carbons, or at least 0.65 per 1000 carbons, or greater than 0.65 per 1000 carbons, or at least 0.70 per 1000 carbons, or greater than 0.70 per 1000 carbons, or at least 0.75 per 1000 carbons, or greater than 0.75 per 1000 carbons.

In an embodiment of the present disclosure, the polyethylene composition is an ethylene homopolymer.

As used herein, the term "homopolymer" is meant to convey its conventional meaning, that the polymer is prepared using only ethylene as a deliberately added polymerizable monomer.

In an embodiment of the present disclosure, the polyethylene composition is a polyethylene copolymer.

In an embodiment of the disclosure, the polyethylene composition is a polyethylene copolymer of ethylene and one or more than one alpha olefin.

Suitable alpha olefin comonomers for polymerization with ethylene to make the polyethylene copolymer include 1-butene, 1-hexene and 1-octene.

Examples of polyethylene homopolymers which are useful in the present disclosure are SCLAIR® 2908 and SCLAIR® 2907 which are commercially available from NOVA Chemicals Corporation. Examples of polyethylene copolymers which are useful in the present disclosure are SCLAIR 2710 and SCLAIR 2807 which are commercially available from NOVA Chemicals Corporation.

In an embodiment of the disclosure, the polyethylene copolymer comprises from about 0.1 to about 5 weight %, in some cases less than about 3 weight %, in other instances less than about 1.5 weight % of an alpha olefin selected from 1-butene, 1-hexene, 1-octene and mixtures thereof.

In an embodiment of the disclosure, the polyethylene copolymer comprises polymerized ethylene and 1-butene.

In an embodiment of the disclosure, the polyethylene copolymer has a density of from about 0.945 to about 0.960 g/cm$^3$ as determined according to ASTM D 792. In other embodiments of the disclosure, the polyethylene copolymer has a density of from about 0.948 to about 0.958 g/cm$^3$, or from about 0.949 g/cm$^3$ to about 0.955 g/cm$^3$.

Examples of polyethylene copolymers which are useful in the present disclosure include by way of non-limiting example, SCLAIR 2710, and SCLAIR 2807, each of which is commercially available from NOVA Chemicals Corporation.

In an embodiment of the disclosure, the polyethylene homopolymer has a density from about 0.955 to about 0.967 g/cm$^3$ as determined according to ASTM D 792. In other embodiments of the disclosure, the polyethylene homopolymer has a density of from about 0.958 to about 0.965 g/cm$^3$, or from about 0.958 to about 0.963 g/cm$^3$, or from about 0.959 to about 0.963 g/cm$^3$.

Examples of polyethylene homopolymers which are useful in the present disclosure include by way of non-limiting example, SCLAIR 2907, and SCLAIR 2908, each of which is commercially available from NOVA Chemicals Corporation.

In an embodiment of the disclosure, the polyethylene compositions suitable for use in the present disclosure may be prepared using conventional polymerization processes, non-limiting examples of which include gas phase, slurry phase and solution phase polymerization processes. Such processes are well known to those skilled in the art.

In an embodiment of the disclosure, the polyethylene composition may be prepared using conventional polymerization catalysts. Some non-limiting examples of conventional polymerization catalysts include chrome based catalysts and Ziegler-Natta catalysts. Such catalysts are well known to those skilled in the art.

In some embodiments, solution and slurry phase polymerization processes are conducted in the presence of an inert hydrocarbon solvent/diluent, such as for example, a $C_{4-12}$ hydrocarbon which may be unsubstituted or substituted by a $C_{1-4}$ alkyl group, such as, butane, pentane, hexane, heptane, octane, cyclohexane, methylcyclohexane or hydrogenated naphtha. A non-limiting example of a commercial solvent is ISOPAR™ E ($C_{8-12}$ aliphatic solvent, Exxon Chemical Co.). The monomers are dissolved in the solvent/diluent.

A slurry polymerization process may be conducted at temperatures of from about 20° C. to about 180° C., or from 80° C. to about 150° C., and the polyethylene composition being made is insoluble in the liquid hydrocarbon diluent.

A solution polymerization process may be conducted at temperatures of from about 180° C. to about 250° C., or from about 180° C. to about 230° C., and the polyethylene composition being made is soluble in the liquid hydrocarbon phase (e.g., the solvent).

A gas phase polymerization process can be carried out in either a fluidized bed or a stirred bed reactor. A gas phase polymerization typically involves a gaseous mixture comprising from about 0 to about 15 mole % of hydrogen, from about 0 to about 30 mole % of one or more $C_{3-8}$ alpha-olefins, from about 15 to about 100 mole % of ethylene, and from about 0 to about 75 mole % of an inert gas at a temperature from about 50° C. to about 120° C., or from about 75° C. to about 110° C.

Suitable alpha olefins which may be polymerized with ethylene in the case of a polyethylene copolymer are $C_{3-8}$ alpha olefins such as one or more of 1-butene, 1-hexene, and 1-octene.

In an embodiment of the disclosure, the polyethylene composition is made in a solution phase polymerization reactor.

In an embodiment of the disclosure, the polyethylene composition is prepared by contacting ethylene and optionally an alpha-olefin with a polymerization catalyst under solution polymerization conditions.

In an embodiment of the disclosure, the polyethylene composition is made with a Ziegler-Natta polymerization catalyst.

In an embodiment of the disclosure, the polyethylene composition is made in a single solution phase polymerization reactor.

In an embodiment of the disclosure, the polyethylene composition is made in a solution polymerization process using a Ziegler-Natta catalyst.

In an embodiment of the disclosure, the polyethylene composition is made in a single solution phase polymerization reactor using a Ziegler-Natta catalyst.

The term "Ziegler-Natta" catalyst is well known to those skilled in the art and is used herein to convey its conventional meaning. Ziegler-Natta catalysts are polymerization catalysts comprising at least one transition metal compound of a transition metal selected from groups 3, 4, or 5 of the Periodic Table (using IUPAC nomenclature) and an organoaluminum component that is defined by the formula:

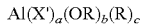

$$Al(X')_a(OR)_b(R)_c$$

wherein: X' is a halide (for example, chlorine); OR is an alkoxy or aryloxy group; R is a hydrocarbyl (for example, an alkyl having from 1 to 10 carbon atoms); and a, b, or c are each 0, 1, 2, or 3 with the provisos, a+b+c=3 and b+c≥1. As will be appreciated by those skilled in the art of ethylene polymerization, conventional Ziegler-Natta catalysts may also incorporate additional components, such as, an electron donor. For example, an amine or a magnesium compound or a magnesium alkyl such as butyl ethyl magnesium and a halide source (which is, in some embodiments, a chloride, such as, tertiary butyl chloride). Such components, if employed, may be added to the other catalyst components prior to introduction to the reactor or may be added directly to the reactor. The Ziegler-Natta catalyst may also be "tempered" (i.e. heat treated) prior to being introduced to the reactor (again, using techniques which are well known to those skilled in the art and published in the literature).

In an embodiment of the disclosure, the polyethylene composition has ≤1.5 ppm, or ≤1.3 ppm, or ≤1.0 ppm, or ≤0.9 ppm, or ≤0.8, or ≤0.8 ppm, or ≤0.75 ppm, or 0.50 ppm of titanium (Ti) present.

In an embodiment of the disclosure, the polyethylene composition has ≤1.5 ppm, or ≤1.3 ppm, or ≤1.0 ppm, or ≤0.9 ppm, or ≤0.8 ppm, or ≤0.75, or ≤0.60 ppm of aluminum (Al) present.

In an embodiment of the disclosure, the polyethylene composition has ≤0.5 ppm, or 0.4 ppm, or ≤0.3 ppm, or ≤0.2 ppm, or ≤0.15 ppm, or ≤0.1 ppm, of chlorine (Cl) present.

In an embodiment of the disclosure, the polyethylene composition has ≤4.0 ppm, or ≤3.0 ppm, or ≤2.5 ppm, or ≤2.0 ppm, of magnesium (Mg) present.

In an embodiment of the disclosure, the polyethylene composition has ≤0.4 ppm, or ≤0.3 ppm, or ≤0.25 ppm, or ≤0.20 ppm, of chromium (Cr) present.

In an embodiment of the disclosure, the polyethylene composition comprises one or more nucleating agents.

In an embodiment of the disclosure, the polyethylene composition comprises a nucleating agent or a mixture of nucleating agents.

The polyethylene composition may be compounded or dry-blended either by a manufacturer or a converter (e.g., the company converting the resin pellets into the final product). The compounded or dry-blended polyethylene compositions may contain fillers, pigments and other additives. In some embodiments, fillers are inert additives, such as, clay, talc, $TiO_2$ and calcium carbonate, which may be added to the polyolefin compositions in amounts from about 0 weight % up to about 50 weight %, in some cases, less than 30 weight % of fillers are added. The compounded or dry-blended polyethylene compositions may contain antioxidants, heat and light stabilizers, such as, combinations of one or more of hindered phenols, phosphates, phosphites and phosphonites, for example, in amounts of less than about 0.5 weight % based on the weight of the polyethylene compositions. Pigments may also be added to the polyethylene polymers in small amounts. Non-limiting examples of pigments include carbon black, phthalocyanine blue, Congo red, titanium yellow, etc.

The polyethylene compositions may contain a nucleating agent or a mixture of nucleating agents in amounts of from about 5 parts per million (ppm) to about 10,000 ppm based on the weight of the polyethylene polymer. The nucleating agent may be selected from dibenzylidene sorbitol, di(p-methyl benzylidene) sorbitol, di(o-methyl benzylidene) sorbitol, di(p-ethylbenzylidene) sorbitol, bis(3,4-dimethyl benzylidene) sorbitol, bis(3,4-diethylbenzylidene) sorbitol and bis(trimethyl-benzylidene) sorbitol. One commercially available nucleating agent is bis(3,4-dimethyl benzylidene) sorbitol.

Optionally, additives can be added to the polyethylene composition. Additives can be added to the polyethylene composition during an extrusion or compounding step, but other suitable known methods will be apparent to a person skilled in the art. The additives can be added as is or added during an extrusion or compounding step. Suitable additives are known in the art and include but are not-limited to antioxidants, phosphites and phosphonites, nitrones, antacids, UV light stabilizers, UV absorbers, metal deactivators, dyes, fillers and reinforcing agents, nano-scale organic or inorganic materials, antistatic agents, lubricating agents such as calcium stearates, slip additives such as erucimide or behenamide, and nucleating agents (including nucleators, pigments or any other chemicals which may provide a nucleating effect to the high density polyethylene composition). The additives that can be optionally added are, for example, added in amount of up to 20 weight percent (wt %).

One or more nucleating agent(s) may be introduced into the polyethylene composition by kneading a mixture of the polymer, usually in powder or pellet form, with the nucleating agent, which may be utilized alone or in the form of a concentrate containing further additives, such as, stabilizers, pigments, antistatics, UV stabilizers and fillers. In an embodiment of the disclosure, a nucleating agent should be a material which is wetted or absorbed by the polymer, which is insoluble in the polymer and of melting point higher than that of the polymer, and it should be homogeneously dispersible in the polymer melt in as fine a form as possible (1 to 10 μm). Compounds known to have a nucleating capacity for polyolefins include salts of aliphatic monobasic or dibasic acids or arylalkyl acids, such as sodium succinate, or aluminum phenylacetate; and alkali metal or aluminum salts of aromatic or alicyclic carboxylic acids such as sodium β-naphthoate, or sodium benzoate.

Examples of nucleating agents which are commercially available and which may be added to the polyethylene composition are dibenzylidene sorbital esters (such as the products sold under the trademark MILLAD® 3988 by Milliken Chemical and IRGACLEAR® by Ciba Specialty Chemicals). Further examples of nucleating agents which may added to the polyethylene composition include the cyclic organic structures disclosed in U.S. Pat. No. 5,981,636 (and salts thereof, such as disodium bicyclo [2.2.1] heptene dicarboxylate); the saturated versions of the structures disclosed in U.S. Pat. No. 5,981,636 (as disclosed in U.S. Pat. No. 6,465,551; Zhao et al., to Milliken); the salts of certain cyclic dicarboxylic acids having a hexahydrophtalic acid structure (or "HHPA" structure) as disclosed in U.S. Pat. No. 6,599,971 (Dotson et al., to Milliken); and phosphate esters, such as those disclosed in U.S. Pat. No. 5,342,868 and those sold under the trade names NA-11 and NA-21 by Asahi Denka Kogyo, cyclic dicarboxylates and the salts thereof, such as the divalent metal or metalloid salts, (particularly, calcium salts) of the HHPA structures disclosed in U.S. Pat. No. 6,599,971. For clarity, the HHPA structure generally comprises a ring structure with six carbon atoms in the ring and two carboxylic acid groups which are substituents on adjacent atoms of the ring structure. The other four carbon atoms in the ring may be substituted, as disclosed in U.S. Pat. No. 6,599,971. An example is 1,2-cyclohexanedicarboxylicacid, calcium salt (CAS registry number 491589-22-1). Still further examples of nucleating agents which may added to the polyethylene composition include those disclosed in WO2015042561, WO2015042563, WO2015042562 and WO 2011050042.

Many of the above described nucleating agents may be difficult to mix with the polyethylene composition that is being nucleated and it is known to use dispersion aids, such as, for example, zinc stearate, to mitigate this problem.

In an embodiment of the disclosure, the nucleating agents are well dispersed in the polyethylene composition.

In an embodiment of the disclosure, the amount of nucleating agent used is comparatively small—from 5 to 3000 parts by million per weight (based on the weight of the polyethylene composition) so it will be appreciated by those skilled in the art that some care must be taken to ensure that the nucleating agent is well dispersed. In an embodiment of the disclosure, the nucleating agent is added in finely divided form (less than 50 microns, especially less than 10 microns) to the polyethylene composition to facilitate mixing. This type of "physical blend" (i.e., a mixture of the nucleating agent and the resin in solid form) is generally preferable to the use of a "masterbatch" of the nucleator (where the term "masterbatch" refers to the practice of first melt mixing the additive—the nucleator, in this case—with a small amount of the polyethylene composition resin—then melt mixing the "masterbatch" with the remaining bulk of the polyethylene composition resin).

In an embodiment of the disclosure, an additive such as nucleating agent may be added to the polyethylene composition by way of a "masterbatch", where the term "masterbatch" refers to the practice of first melt mixing the additive (e.g., a nucleator) with a small amount of the polyethylene composition, followed by melt mixing the "masterbatch" with the remaining bulk of the unimodal polyethylene composition.

In an embodiment of the disclosure, the polyethylene composition further comprises a nucleating agent or a mixture of nucleating agents.

Since the polyethylene composition may be used in closures typically used for food contact applications, the additive package, if present, must meet the appropriate food regulations, such as, the FDA regulations in the United States for such food contact applications.

In an embodiment of the disclosure, the polyethylene compositions described above are used in the formation of molded articles. For example, articles formed by continuous compression molding and injection molding are contemplated. Such articles include, for example, caps, hinged caps, screw caps, closures and hinged closures for bottles.

The Hinged Component

In an embodiment of the disclosure, the polyethylene compositions described herein are used in the formation of a hinged component.

In an embodiment of the disclosure, the hinged component can be a part of a cap or closure or it can be a cap or closure per se.

The hinged component, can be made according to any known method, including for example injection molding and compression molding techniques that are well known to persons skilled in the art. Hence, in an embodiment of the disclosure a hinged component comprising the polyethylene composition defined herein is prepared with a process comprising at least one compression molding step and/or at least one injection molding step.

In an embodiment of the disclosure, the polyethylene compositions described herein are used in a process to make a hinged component. Such processes include, for example, compression molding (or continuous compression molding) and injection molding.

In an embodiment of the disclosure, a hinged component is a component that has at least two bodies which are connected to one another through a flexible hinge. The flexible hinge may be a continuous, partial or segmented section (which is, in some embodiments, thinner than the two or more bodies), so as to act as a fulcrum or pivot point about which the two or more bodies may bend. For example the two or more bodies may bend about the flexible hinge from a molded position into a flexed position.

Examples of hinged components include caps or closures having a single strap, dual strap, multi strap or butterfly strap designs such as, for example, those shown in U.S. Patent Application Publication 2013/0343808 (see, for example, FIGS. 3 to 13 therein).

Another example of a hinged component is provided in U.S. Patent Application Publication No. 2014/0275426.

In an embodiment of the disclosure the hinged component is a hinged cap or closure, or the like for bottles, containers and the like.

Caps and closures may be formed by continuous compression molding or by injection molding. Such closures include, for example, hinged caps, hinged screw caps, hinged snap-top caps, and hinged closures for bottles, containers and the like.

In an embodiment of the disclosure, a hinged component is a closure (or cap) comprising a hinge made of the same material as the rest of the closure (or cap).

In an embodiment of the disclosure, a hinged component is a hinged closure (or cap).

In an embodiment of the disclosure, a hinged component is a hinged closure (or cap) for bottles, containers and the like.

In an embodiment of the disclosure, a hinged component is a flip-top hinge closure, such as a flip-top hinge closure for use on a plastic ketchup bottle or similar containers containing foodstuffs.

When a closure is a hinged closure, it may comprise a hinged component and in some embodiments, comprises at least two bodies which are connected by a thinner section that acts as a hinge allowing the at least two bodies to bend from an initially molded position. The thinner section may, for example, be continuous or web-like, wide or narrow.

A useful hinged component is a hinged closure (for bottles, containers and the like) and may be made of two bodies joined to each other by at least one thinner bendable portion (e.g., the two bodies can be joined by a single bridging portion, or more than one bridging portion, or by a webbed portion, etc.). A first body may contain a dispensing hole and which may snap onto or screw onto a container to cover a container opening (e.g., a bottle opening) while a second body may serve as a snap on lid which may mate with the first body.

Hinged caps and closures can be made according to any known method, including, for example injection molding and compression molding techniques that are well known to persons skilled in the art. Hence, in an embodiment of the disclosure a hinged closure (or cap) comprising the polyethylene composition is prepared with a process comprising at least one continuous compression molding step and/or at least one injection molding step.

The hinged closures and caps of this disclosure may be used for sealing bottles, containers and the like, for example, bottles that may contain drinkable water, and other foodstuffs, including but not limited to liquids that are non-pressurized. The hinged closures and caps may also be used for sealing bottles containing drinkable water or non-carbonated beverages (e.g., juice). Other applications, include hinged caps and closures for bottles and containers containing foodstuffs, such as, for example ketchup bottles and the like.

In an embodiment of the present disclosure, a hinged component has an average hinge life of at least 2,300 cycles.

In an embodiment of the present disclosure, a hinged component has an average hinge life of at least 2,400 cycles.

In an embodiment of the present disclosure, a hinged component has an average hinge life of at least 2,500 cycles.

In an embodiment of the present disclosure, a hinged component has an average hinge life of at least 3,000 cycles.

In an embodiment of the present disclosure, a hinged component has an average hinge life of at least 3,500 cycles.

In an embodiment of the present disclosure, a hinged component has an average hinge life of from about 2,400 cycles to about 10,000 cycles.

In an embodiment of the present disclosure, a hinged component has an average hinge life of from about 2,500 cycles to about 8,000 cycles.

In an embodiment of the present disclosure, a hinged component has an average hinge life of from about 3,000 cycles to about 8,000 cycles.

In an embodiment of the present disclosure, a hinged component has an average hinge life of from about 3,500 cycles to about 10,000 cycles.

In an embodiment of the present disclosure, a hinged component has an average hinge life of from about 3,500 cycles to about 8,000 cycles.

Additional embodiments of the invention are further illustrated by the following non-limiting examples.

Examples

Melt indexes, $I_2$, $I_5$, $I_6$ and $I_{21}$ for the polyethylene composition were measured according to ASTM D1238 (when conducted at 190° C., using a 2.16 kg, a 5 kg, a 6.48 kg and a 21 kg weight respectively).

$M_n$, $M_w$, and $M_z$ (g/mol) were determined by high temperature Gel Permeation Chromatography with differential refractive index detection using universal calibration (e.g., ASTM-D6474-99). GPC data was obtained using an instrument sold under the trade name "Waters 150c", with 1,2,4-trichlorobenzene as the mobile phase at 140° C. The samples were prepared by dissolving the polymer in this solvent and were run without filtration. Molecular weights are expressed as polyethylene equivalents with a relative standard deviation of 2.9% for the number average molecular weight ("Mn") and 5.0% for the weight average molecular weight ("Mw"). The molecular weight distribution (MWD) is the weight average molecular weight divided by the number average molecular weight, $M_w/M_n$. The z-average molecular weight distribution is $M_z/M_n$. Polymer sample solutions (1 to 2 mg/mL) were prepared by heating the polymer in 1,2,4-trichlorobenzene (TCB) and rotating on a wheel for 4 hours at 150° C. in an oven. The antioxidant 2,6-di-tert-butyl-4-methylphenol (BHT) was added to the mixture in order to stabilize the polymer against oxidative degradation. The BHT concentration was 250 ppm. Sample solutions were chromatographed at 140° C. on a PL 220 high-temperature chromatography unit equipped with four Shodex columns (HT803, HT804, HT805 and HT806) using TCB as the mobile phase with a flow rate of 1.0 mL/minute, with a differential refractive index (DRI) as the concentration detector. BHT was added to the mobile phase at a concentration of 250 ppm to protect the columns from oxidative degradation. The sample injection volume was 200 mL. The raw data were processed with CIRRUS® GPC software. The columns were calibrated with narrow distribution polystyrene standards. The polystyrene molecular weights were converted to polyethylene molecular weights using the Mark-Houwink equation, as described in the ASTM standard test method D6474.

Primary melting peak (° C.), heat of fusion (J/g) and crystallinity (%) was determined using differential scanning calorimetry (DSC) as follows: the instrument was first calibrated with indium; after the calibration, a polymer specimen is equilibrated at 0° C. and then the temperature was increased to 200° C. at a heating rate of 10° C./min; the melt was then kept isothermally at 200° C. for five minutes; the melt was then cooled to 0° C. at a cooling rate of 10° C./min and kept at 0° C. for five minutes; the specimen was then heated to 200° C. at a heating rate of 10° C./min. The DSC Tm, heat of fusion and crystallinity are reported from the $2^{nd}$ heating cycle.

The short chain branch frequency (SCB per 1000 carbon atoms) of the polyethylene composition was determined by Fourier Transform Infrared Spectroscopy (FTIR) as per the ASTM D6645-01 method. A Thermo-Nicolet™ 750 Magna-IR Spectrophotometer equipped with OMNIC® version 7.2a software was used for the measurements. Unsaturations in the polyethylene composition were also determined by Fourier Transform Infrared Spectroscopy (FTIR) as per ASTM D3124-98. Comonomer content can also be measured using $^{13}C$ NMR techniques as discussed in Randall, Rev. Macromol. Chem. Phys., C29 (2&3), p 285; U.S. Pat. No. 5,292,845 and WO 2005/121239.

Polyethylene composition density (g/cm³) was measured according to ASTM D792.

Hexane extractables were determined according to ASTM D5227.

Shear viscosity was measured by using a Kayeness WinKARS Capillary Rheometer (model # D5052M-115). For the shear viscosity at lower shear rates, a die having a die diameter of 0.06 inch and L/D ratio of 20 and an entrance angle of 180 degrees was used. For the shear viscosity at higher shear rates, a die having a die diameter of 0.012 inch and L/D ratio of 20 was used.

To determine CDBI (50), a solubility distribution curve is first generated for the polyethylene composition. This is accomplished using data acquired from the TREF technique. This solubility distribution curve is a plot of the weight fraction of the copolymer that is solubilized as a function of temperature. This is converted to a cumulative distribution curve of weight fraction versus comonomer content, from which the CDBI (50) is determined by establishing the weight percentage of a copolymer sample that has a comonomer content within 50% of the median comonomer content on each side of the median (See WO 93/03093 and U.S. Pat. No. 5,376,439). The CDBI (25) is determined by establishing the weight percentage of a copolymer sample that has a comonomer content within 25% of the median comonomer content on each side of the median The temperature rising elution fractionation (TREF) method used herein was as follows. Polymer samples (50 to 150 mg) were introduced into the reactor vessel of a crystallization-TREF unit (Polymer Char). The reactor vessel was filled with 20 to 40 ml 1,2,4-trichlorobenzene (TCB), and heated to the desired dissolution temperature (e.g., 150° C.) for 1 to 3 hours. The solution (0.5 to 1.5 ml) was then loaded into the TREF column filled with stainless steel beads. After equilibration at a given stabilization temperature (e.g. 110° C.) for 30 to 45 minutes, the polymer solution was allowed to crystallize with a temperature drop from the stabilization temperature to 30° C. (0.1 or 0.2° C./minute). After equilibrating at 30° C. for 30 minutes, the crystallized sample was eluted with TCB (0.5 or 0.75 mL/minute) with a temperature ramp from 30° C. to the stabilization temperature (0.25 or 1.0° C./minute). The TREF column was cleaned at the end of the run for 30 minutes at the dissolution temperature. The data were processed using Polymer Char software, Excel spreadsheet and TREF software developed in-house.

High temperature GPC equipped with an online FTIR detector (GPC-FTIR) was used to measure the comonomer content as the function of molecular weight.

Plaques molded from the polyethylene compositions were tested according to the following ASTM methods: Bent Strip Environmental Stress Crack Resistance (ESCR) at Condition B at 10% and 100% IGEPAL at 50° C., ASTM D1693; notched Izod impact properties, ASTM D256; Flexural Properties, ASTM D 790; Tensile properties, ASTM D 638; Vicat softening point, ASTM D 1525; Heat deflection temperature, ASTM D 648.

Dynamic mechanical analyses were carried out with a rheometer, namely Rheometrics Dynamic Spectrometer (RDS-II) or Rheometrics SR5 or ATS Stresstech, on compression molded samples under nitrogen atmosphere at 190° C., using 25 mm diameter cone and plate geometry. The oscillatory shear experiments were done within the linear viscoelastic range of strain (10% strain) at frequencies from 0.05 to 100 rad/s. The values of storage modulus (G'), loss modulus (G"), complex modulus (G*) and complex viscosity ($\eta'$) were obtained as a function of frequency. The same rheological data can also be obtained by using a 25 mm diameter parallel plate geometry at 190° C. under nitrogen atmosphere.

Example 1 is a hinged component made from a unimodal polyethylene homopolymer having a melt index $I_2$ of 5 g/10 min, a density of 0.960 g/cm$^3$, and a molecular weight distribution Mw/Mn of 2.67. The unimodal polyethylene homopolymer used in Example 1, was made using a Ziegler-Natta catalyst in a solution olefin polymerization process. This resin is commercially available from NOVA Chemicals Corporation as SCLAIR 2907. A GPC profile for the resin is given in FIG. 1.

Figure 2:
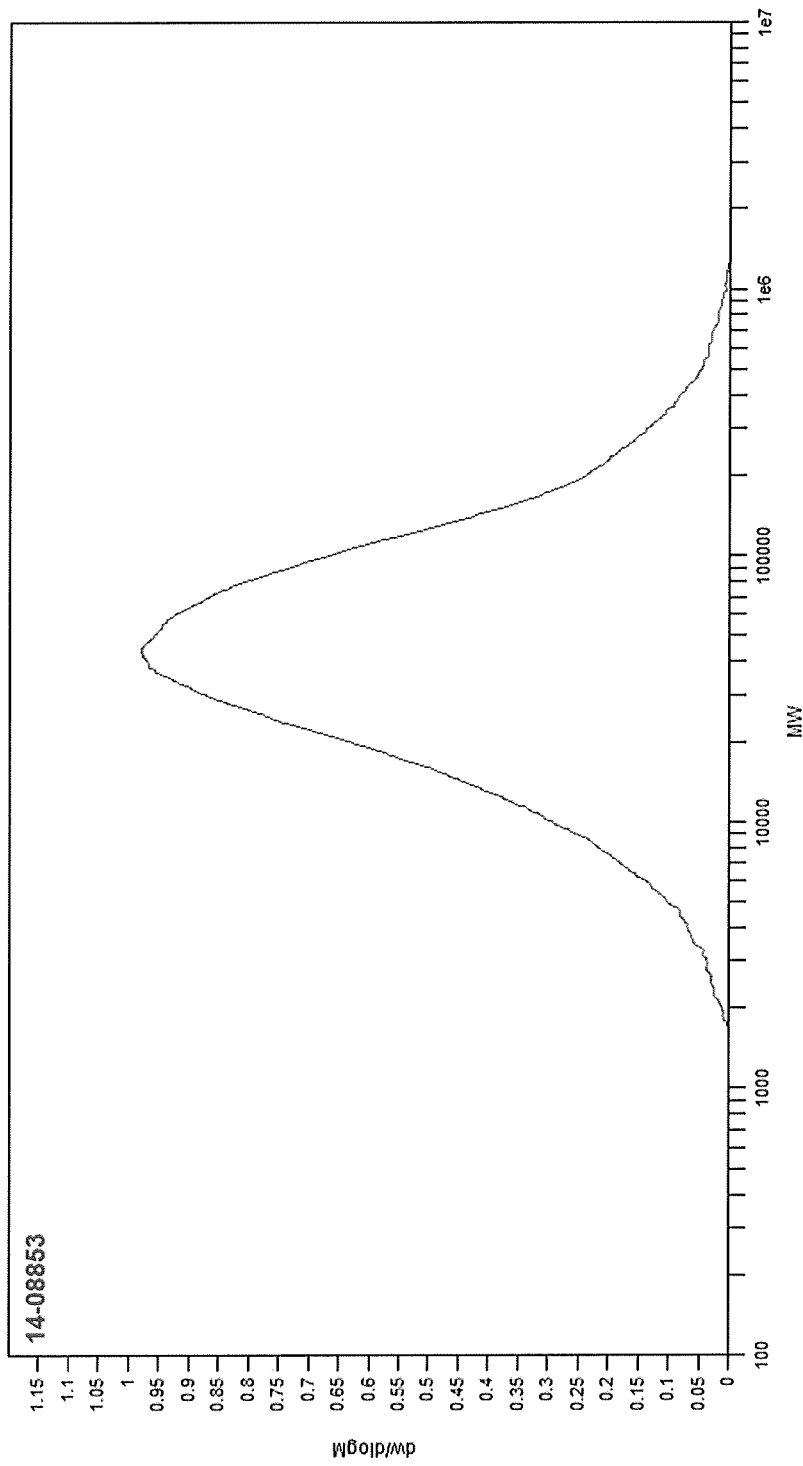
Figure 3:
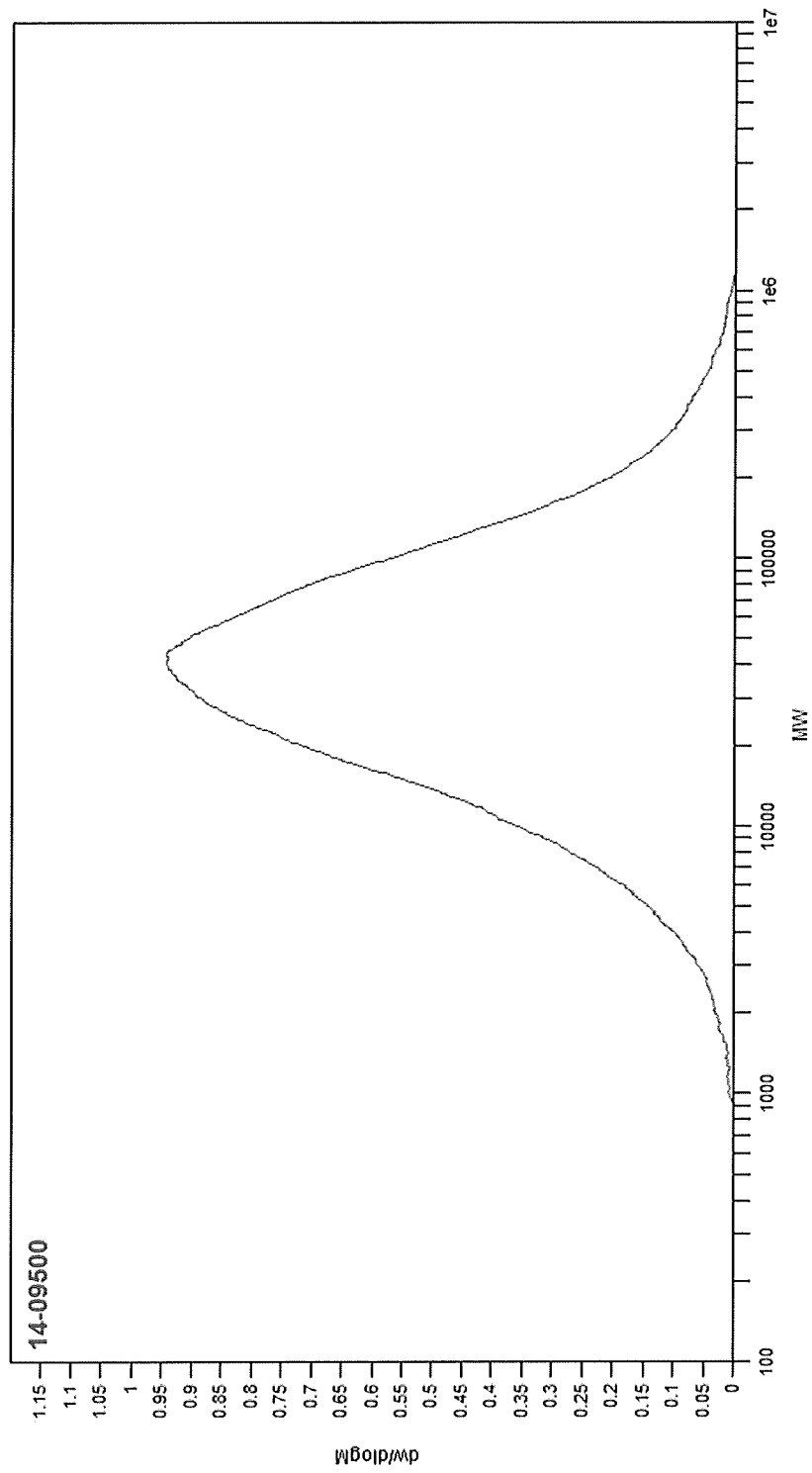
Figure 4:
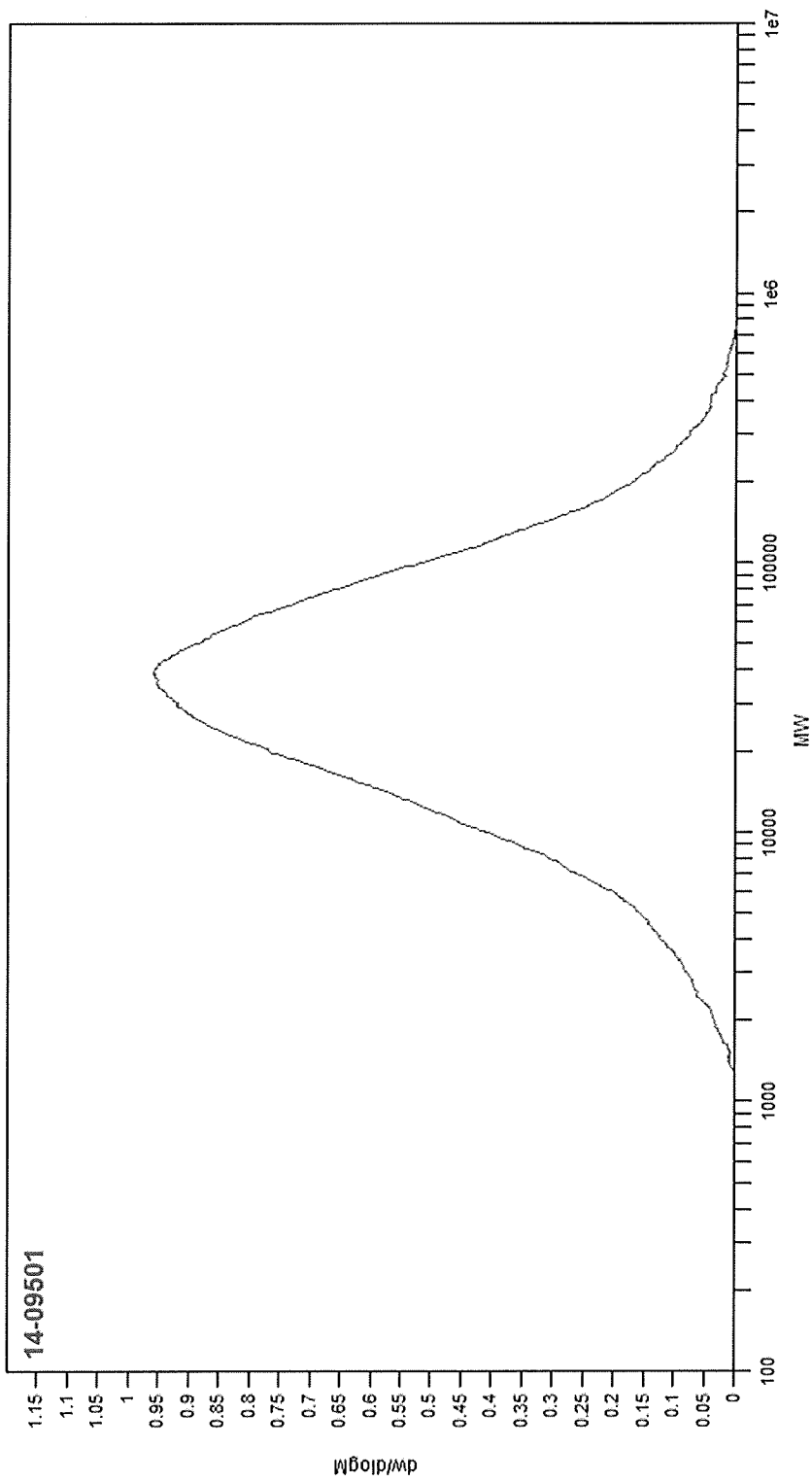
Figure 5:
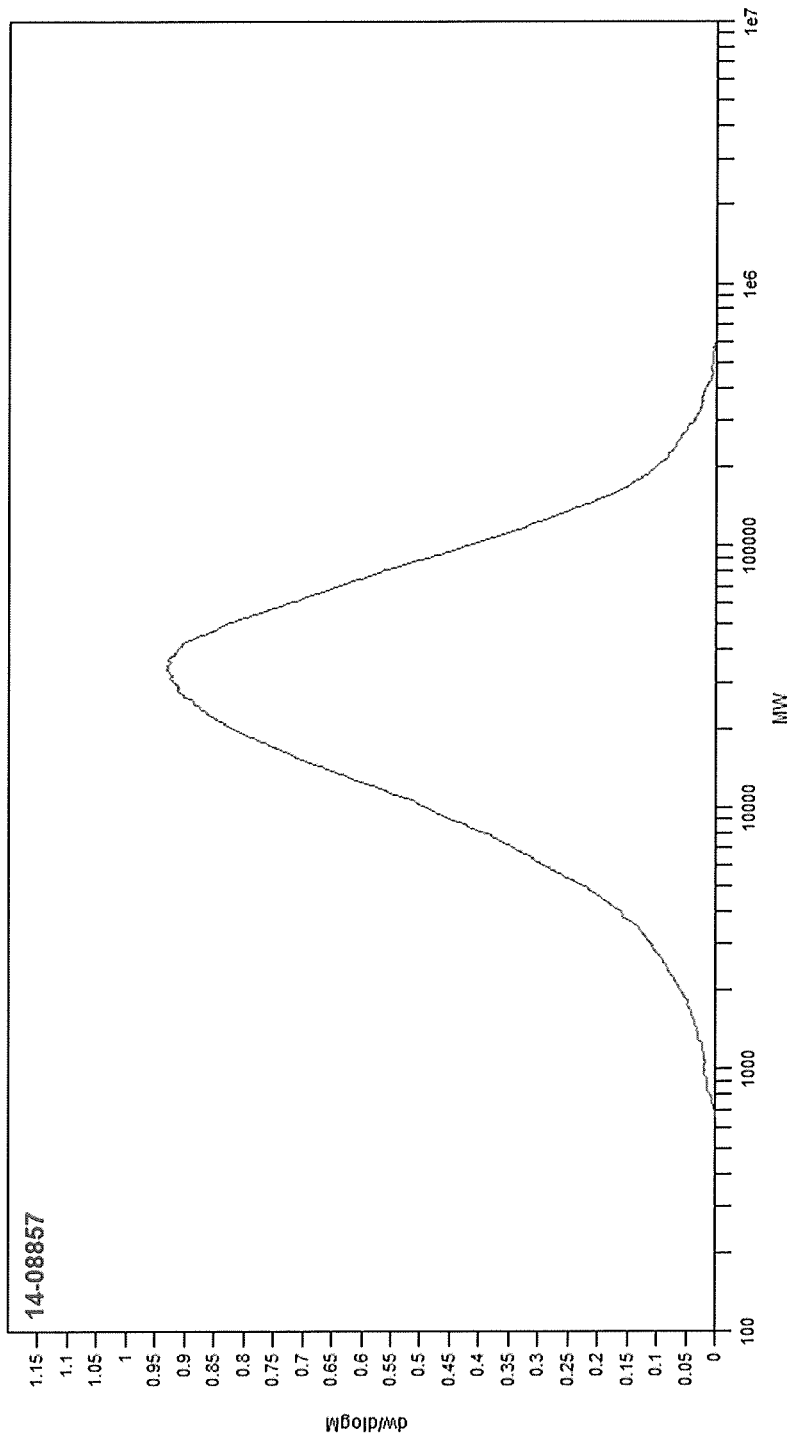

Example 2 is a hinged component made from a unimodal polyethylene copolymer having a melt index $I_2$ of 6.7 g/10 min, a density of 0.954 g/cm$^3$, and a molecular weight distribution Mw/Mn of 2.72. The unimodal polyethylene copolymer used in Example 2, was made using a Ziegler-Natta catalyst in a solution olefin polymerization process. This resin is commercially available from NOVA Chemicals Corporation as SCLAIR 2807. A GPC profile for the resin is given in FIG. 2.

Example 3 is a hinged component made from a unimodal polyethylene homopolymer having a melt index $I_2$ of 10 g/10 min, a density of 0.961 g/cm$^3$, and a molecular weight distribution Mw/Mn of 2.99. The unimodal polyethylene homopolymer used in Example 3, was made using a Ziegler-Natta catalyst in a solution olefin polymerization process. This resin is commercially available from NOVA Chemicals Corporation as SCLAIR 2908. A GPC profile for the resin is given in FIG. 3.

Example 4 is a hinged component made from a unimodal polyethylene copolymer having a melt index $I_2$ of 17 g/10 min, a density of 0.951 g/cm$^3$, and a molecular weight distribution Mw/Mn of 2.72. The unimodal polyethylene copolymer used in Example 4, was made using a Ziegler-Natta catalyst in a solution olefin polymerization process. This resin is commercially available from NOVA Chemicals Corporation as SCLAIR 2710. A GPC profile for the resin is given in FIG. 4.

Example 5 (Comparative) is a hinged component made from a unimodal polyethylene copolymer having a melt index $I_2$ of 32 g/10 min, a density of 0.951 g/cm$^3$, and a molecular weight distribution, Mw/Mn of 2.88, and which is made using a Ziegler-Natta catalyst in a solution olefin polymerization process. This resin is commercially available from NOVA Chemicals Corporation as SCLAIR 2712. A GPC profile for the resin is given in FIG. 5.

Further details of the polymers used to make hinged components in Examples 1-5 are shown in Table 1, along with their plaque data.

TABLE 1

| | | | | | |
|---|---|---|---|---|---|
| Resin and Plaque Properties | | | | | |
| Example No. | 1 | 2 | 3 | 4 | 5 |
| Density (g/cm$^3$) | 0.960 | 0.954 | 0.961 | 0.951 | 0.951 |
| Rheology/Flow Properties | | | | | |
| Melt Index $I_2$ (g/10 min) | 5 | 6.7 | 10 | 17 | 32 |
| Melt Flow Ratio ($I_{21}/I_2$) | 27 | 28.2 | 25.7 | 24 | 22.7 |
| Stress Exponent | 1.32 | 1.33 | 1.29 | 1.27 | 1.24 |
| Shear Viscosity at $10^5$ s$^{-1}$ (240° C., Pa-s) | 7.00 | 7.4 | 7.1 | 6.00 | 5.90 |
| Shear Viscosity Ratio $\eta(10\ s^{-1})/\eta(1000\ s^{-1})$ at 240° C. | 4.21 | 3.82 | 3.72 | 1.66 | 1.49 |
| Shear Viscosity Ratio $\eta(100\ s^{-1})/\eta(1000\ s^{-1})$ at 240° C. | 75 | 59.4 | 58 | 19.62 | |
| GPC - conventional | | | | | |
| $M_n$ | 27405 | 26005 | 21120 | 19622 | 14928 |
| $M_w$ | 73262 | 70836 | 63069 | 53372 | 43003 |
| $M_z$ | 183608 | 185530 | 172700 | 123854 | 95318 |
| Polydispersity Index ($M_w/M_n$) | 2.67 | 2.72 | 2.99 | 2.72 | 2.88 |
| $M_z/M_w$ | 2.51 | 2.62 | 2.74 | 2.32 | 2.22 |

TABLE 1-continued

| | Resin and Plaque Properties | | | | |
|---|---|---|---|---|---|
| Example No. | 1 | 2 | 3 | 4 | 5 |
| Branch Frequency - FTIR (uncorrected for chain end —$CH_3$) | | | | | |
| Uncorrected SCB/1000 C Uncorrected comonomer content (mol %) | | <0.5 | | 0.7 | 1.3 |
| Internal unsaturation (/1000 C) | 0.030 | 0.040 | 0.030 | 0.060 | 0.080 |
| Side chain unsaturation (/1000 C) | 0.030 | 0.030 | 0.030 | 0.050 | 0.050 |
| Terminal unsaturation (/1000 C) | 0.720 | 0.720 | 0.710 | 0.790 | 0.850 |
| Comonomer | — | 1-butene | — | 1-butene | 1-butene |
| TREF $CDBI_{50}$ (%) | — | 78.8 | — | 72.8 | 68.7 |
| TREF $CDBI_{25}$ (%) | — | 66.9 | — | 59.6 | 50.5 |
| DSC | | | | | |
| Primary Melting Peak (° C.) | 132.13 | 130.04 | 131.92 | 127.75 | 126.99 |
| Heat of Fusion (J/g) | 226.30 | 215.7 | 228.7 | 205.40 | 210.40 |
| Crystallinity (%) | 78.05 | 74.37 | 78.87 | 70.82 | 72.55 |
| Environmental Stress Crack Resistance | | | | | |
| ESCR Cond. B at 100% (hours) | 3 | 3 | 3 | 2 | 0 |
| ESCR Cond. B at 10% (hours) | 4 | 3 | 3 | 1 | 0 |
| Flexural Properties (Plaques) | | | | | |
| Flex Secant Mod. 2% (MPa) | 1018 | 886 | 1080 | 787 | 786 |
| Impact Properties (Plaques) | | | | | |
| Izod Impact (ft-lb/in) | 0.80 | 1.13 | 1.20 | 0.76 | 0.66 |
| Other properties | | | | | |
| Hexane Extractables (weight %) | 0.21 | 0.24 | 0.23 | 0.33 | 0.43 |
| VICAT Soft. Pt. (° C.) - Plaque | 129 | 127 | 128.3 | 123.9 | 122 |
| Heat Deflection Temp. [° C.] @ 66 PSI | 75 | 74 | 77.3 | 65.4 | 66 |

The polymer compositions of Examples 1-5 were injection molded into hinge components as further described below.

The Hinged Component

A four-cavity hinged component mold was used which can produce four types of hinged component. These four hinged components may have different geometries and dimensions which are designed to simulate the hinge sections of typical hinged caps and closures. Among the four types of hinged components, hinge component, "hinge number 4" was used in the present analysis. The design and dimensions of hinge No. 4 are provided in FIGS. 6-8.

Injection Molding Conditions

The four-cavity hinge component mold described above is used in a Sumitomo injection molding machine (model SE75EV C250M, 28 mm screw diameter). The injection molding processing conditions are given in Table 2.

TABLE 2

| | Injection Molding Parameters | | | | |
|---|---|---|---|---|---|
| Example No. | 1 | 2 | 3 | 4 | 5 |
| Part Weight (g) | 10.1 | 10.1 | 10.1 | 10.1 | 10.0 |
| Injection Speed (mm/s) | 135 | 135 | 135 | 135 | 135 |
| Cycle time (s) | 19.567 | 19.568 | 19.569 | 19.568 | 19.57 |
| Filling time (s) | 0.2212 | 0.2213 | 0.2212 | 0.2211 | 0.2209 |
| Dosing time (s) | 4.219 | 4.233 | 4.224 | 4.26 | 4.468 |
| Minimum Cushion (mm) | 4.755 | 4.963 | 4.867 | 5.845 | 6.271 |
| Filling peak pressure (psi) | 19804.4 | 19447.6 | 18518.6 | 16475.4 | 14208 |
| Full peak pressure (psi) | 19816.8 | 19456.2 | 18531.3 | 16475.4 | 14208 |
| Hold end position (mm) | 4.755 | 4.963 | 4.867 | 5.845 | 6.301 |
| Hold pressure set (psi) | 16500 | 16000 | 15500 | 13500 | 11500 |
| Clamp force (ton) | 50.31 | 49.85 | 49.74 | 49.63 | 49.14 |
| Fill start position (mm) | 38.506 | 38.506 | 38.506 | 38.506 | 38.506 |
| Dosing back pressure (psi) | — | — | 1944.6 | 1689.8 | 1408.1 |
| Pack pressure (psi) | 2094.8 | 2021.5 | 13754.2 | 11671.8 | 9896.4 |
| Filling time 1 (s) | 0.224 | 0.224 | 0.224 | 0.224 | 0.2209 |
| Temperature zone 1 (° C.) | 230 | 230 | 230 | 230 | 230 |
| Temperature zone 2 (° C.) | 235 | 235 | 235 | 235 | 235 |
| Temperature zone 3 (° C.) | 240 | 240 | 240 | 240 | 240 |
| Temperature zone 4 (° C.) | 250 | 250 | 250 | 250 | 250 |

TABLE 2-continued

| Injection Molding Parameters | | | | | |
|---|---|---|---|---|---|
| Example No. | 1 | 2 | 3 | 4 | 5 |
| Temperature zone 5 (° C.) | 250 | 250 | 250 | 250 | 250 |
| Mold temperature stationary (° C.) | 10 | 10 | 10 | 10 | 10 |
| Mold temperature moving (° C.) | 10 | 10 | 10 | 10 | 10 |

The Hinge Life Test

Figure 6:
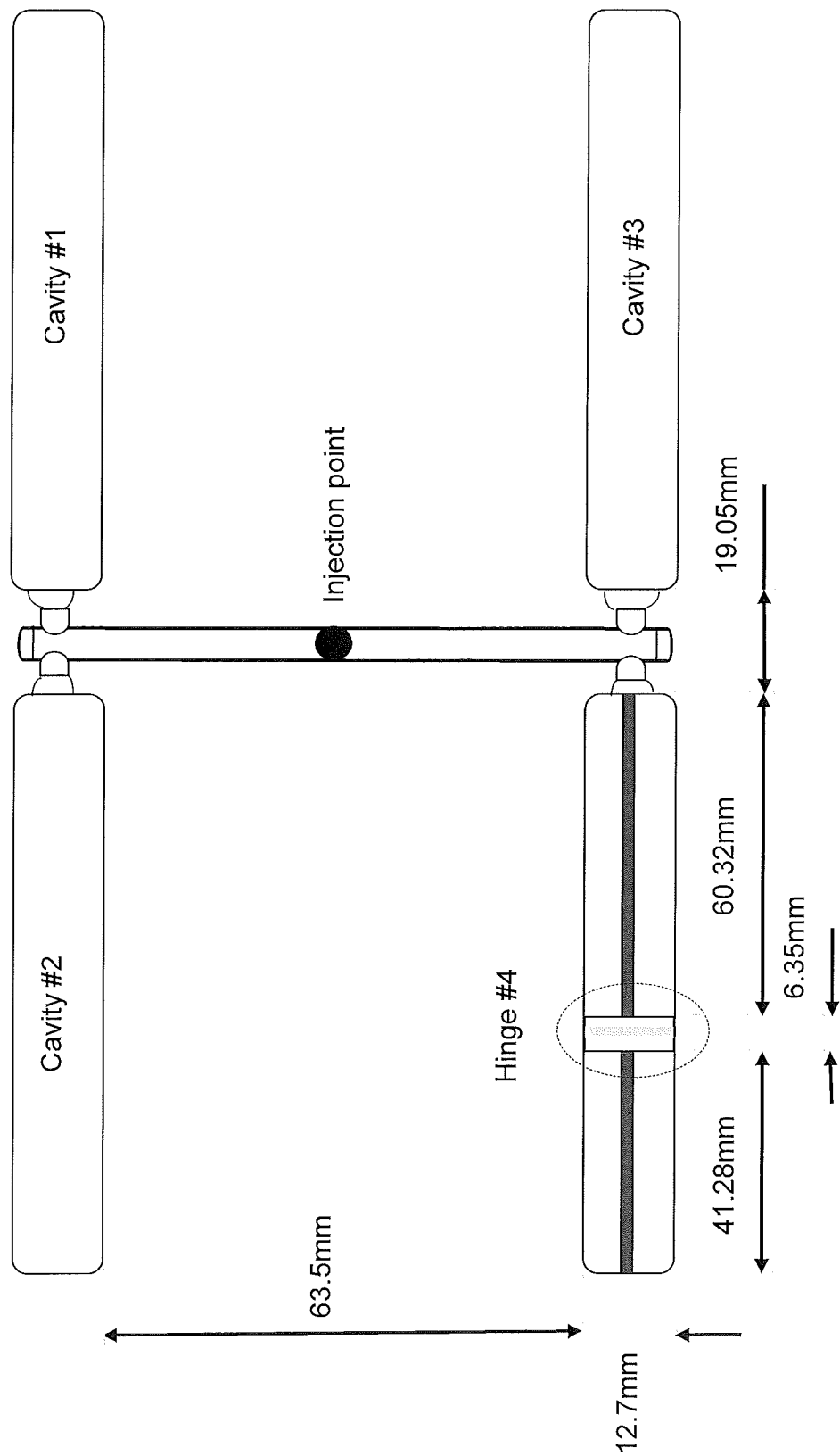
FIG. 6 shows an illustration of a four cavity hinge component mold along with some dimensions of the hinge component, "hinge no. 4". Hinge component, "hinge no. 4" was used for hinge component life cycle testing.
Figure 7:
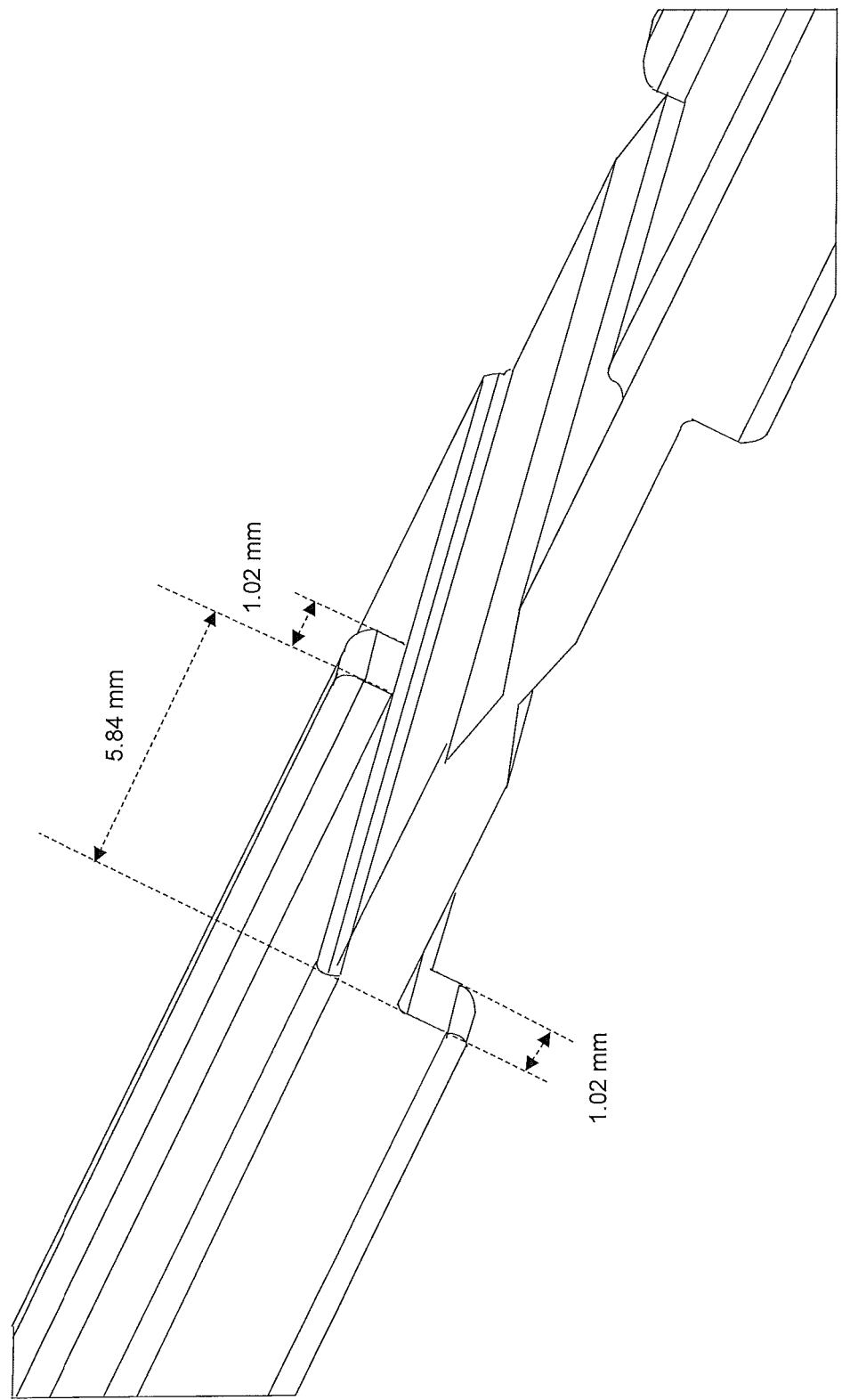
FIG. 7 shows an expanded perspective view of the hinge area of the hinge component, "hinge no. 4" along with some of its dimensions.
Figure 8:
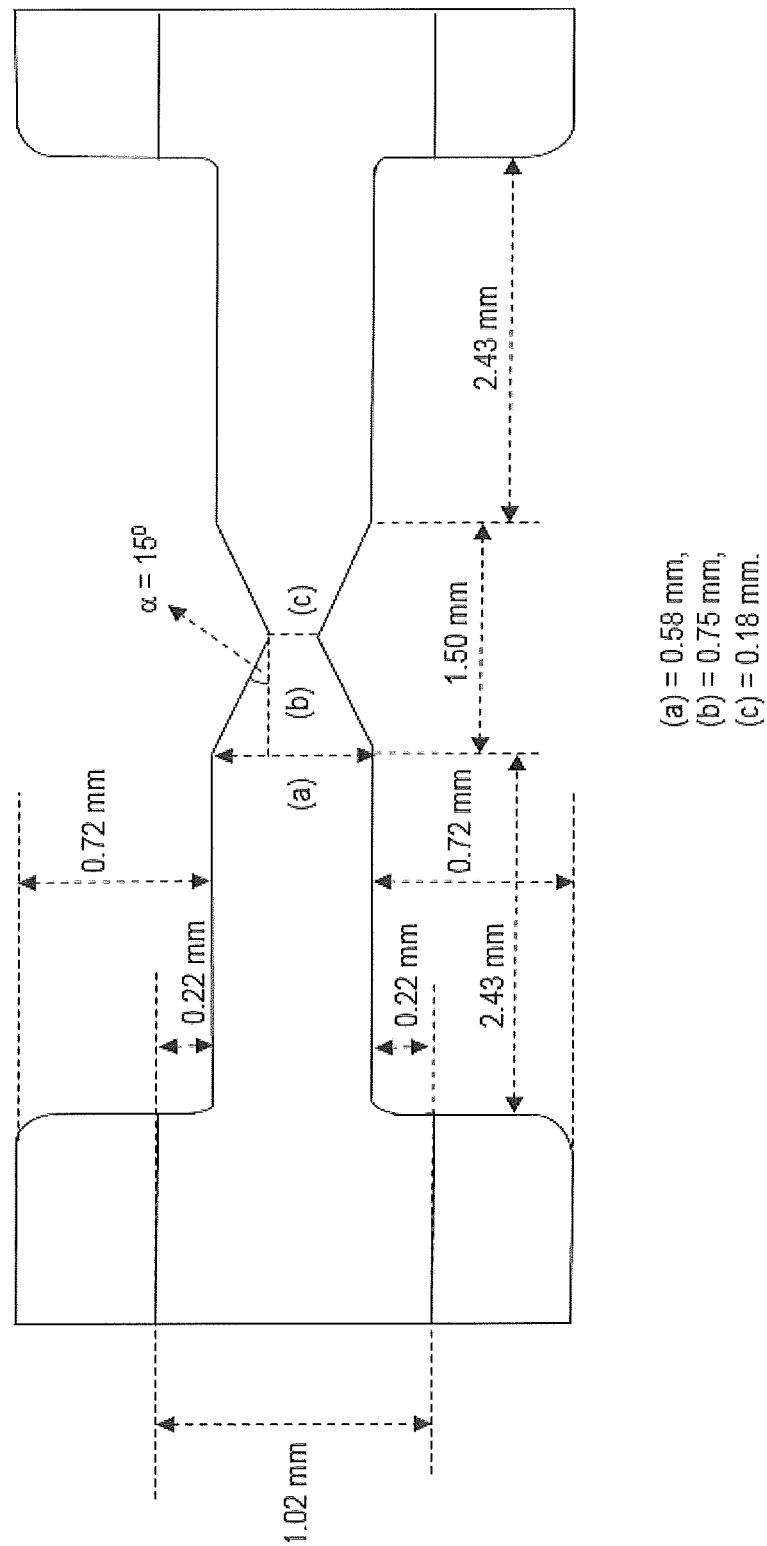
FIG. 8 shows an expanded side view illustration of the hinge component, "hinge no. 4" along with some dimensions and the angle, α which is equal to 15°.

After injection molding and conditioning at room temperature for at least 72 hours, the hinge number 4 was isolated from the mold and used directly in a so called "hinge component life test". The hinged component dimensions were as shown in FIGS. 6-8. Generally, the test involves bending the hinged component from an unstressed, unbent position about its hinge axis and through an angle of about 130° and then allowing the hinged component to return to an unstressed position. The device used to carry out the testing in shown in FIGS. 9 and 10.

Figure 9:
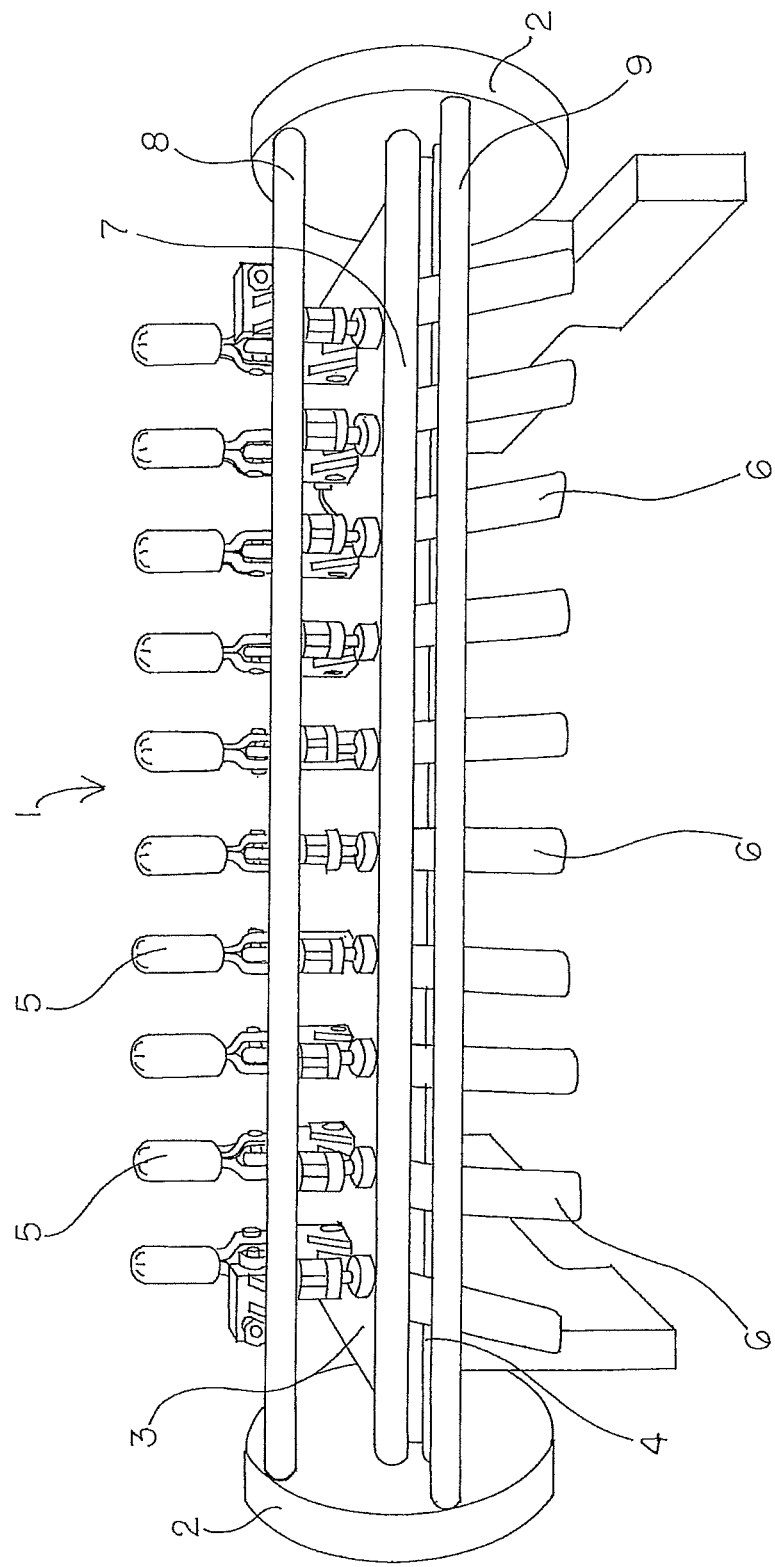
FIG. 9 shows a front perspective view of the device 1, used to measure the average hinge life values of a hinged component.
Figure 10:
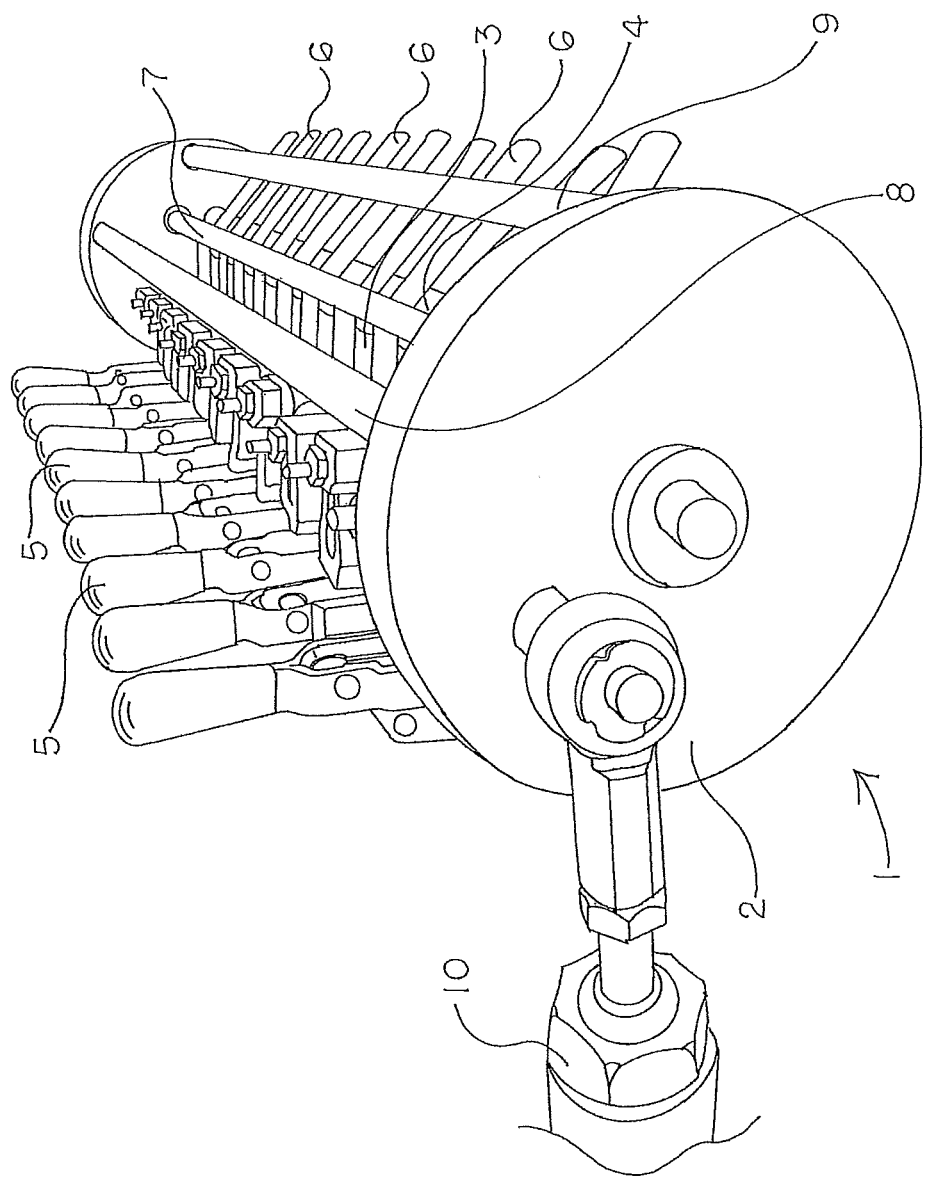
FIG. 10 shows a side perspective view of the device 1, used to measure the average hinge life values of a hinged component.

The device 1 comprises a pair of rotating end disks 2 which encompass a flat plate area 3 between them. The plate has a rounded edge or lip. On the top of the plate area is fixed a series of clamps 5 positioned adjacent to the plate edge. The clamps secure one end of the hinged component onto the plate surface, with the component's hinge axis (or desired location of bending) aligned with the plate edge (note: with reference to FIGS. 6 and 10, the clamp is placed at the longitudinal mid-point of the short side of the hinge component, hinge number 4, shown as element 6 in FIGS. 9 and 10). Hence, the hinged component is clamped on one side of the device as shown in FIGS. 9 and 10 with the hinge axis aligned with the plate edge over which it is to be bent. The other end of the hinged component extends between two lateral bars 4 and 7 which are positioned beyond the hinge axis and which ride over (bar 7) and under (bar 4) the unclamped end of the hinged component. A second set of bars 8 and 9 help to provide structural rigidity to the device. The bars are attached to the rotating end disks, which when rotated, force the upper bar 7 down on the unclamped end of the hinged component bending the hinged component about its hinge axis through an angle of about 130°. This downward bending motion followed by removal of bending stress is considered one cycle (note: after the first bend, the hinge component does not fully return to its original un-bent position). The hinged component is subject to repeated cycles of being bent then allowed to relax. The hinge component testing device was operated at a bending frequency of 45 cycles per minute. The cycles were repeated until the hinged component failed. An electronic counter, for example, one which has an actuator that comes in contact with a protuberance on the outside surface of an end disk, may be used in conjunction with the device. A video camera may also be mounted near the device to record the exact cycle count at which a hinge component break occurs. As the device has several areas to clamp a hinged component for side by side testing, ten hinged components being made of the same polymer composition were tested at the same time (see FIGS. 9 and 10). Generally, a total of 20 to 30 hinge component specimens were tested for a given polymer composition. The average number of cycles before the hinge failed and the standard deviations of the hinge life were then calculated and reported for a given polymer composition. The hinge component life test then reports the average number of cycles endured by a hinged component made from a given polymer composition before failure. The rotating end disks may be rotated manually or as show in FIG. 10 they may be driven by a hydraulic piston, 10. The results of such testing is provided in Table 3. The hinge life cycle data for hinged components made from the polyethylene compositions of Examples 1-5 are given in Table 3.

TABLE 3

| Hinge Life in No. of Cycles | | | | | |
|---|---|---|---|---|---|
| Example No. | 1 | 2 | 3 | 4 | 5 |
| Average | 4550 | 4331 | 3674 | 4928 | 2248 |
| Standard deviation | 550 | 370 | 330 | 373 | 224 |
| Sample Size, n | 30 | 30 | 30 | 30 | 30 |

A comparison between the hinged components made from the polyethylene compositions of Examples 1-4, each of which have a melt index $I_2$ of substantially below 30 g/10 min and a hinged component made with the polyethylene composition of Example 5 which has a melt index $I_2$ of greater than 30 g/10 min shows that Examples 1-4 have much better hinge life cycle values.

Neutron Activation Analysis (NAA)

Neutron Activation Analysis, hereafter NAA, was used to determine catalyst residues in ethylene polymers and was performed as follows. A radiation vial (composed of ultrapure polyethylene, 7 mL internal volume) was filled with an ethylene polymer product sample and the sample weight was recorded. Using a pneumatic transfer system the sample was placed inside a SLOWPOKE™ nuclear reactor (Atomic Energy of Canada Limited, Ottawa, Ontario, Canada) and irradiated for 30 to 600 seconds for short half-life elements (e.g., Ti, V, Al, Mg, and Cl) or 3 to 5 hours for long half-life elements (e.g., Zr, Hf, Cr, Fe and Ni). The average thermal neutron flux within the reactor was $5 \times 10^{11}/cm^2/s$. After irradiation, samples were withdrawn from the reactor and aged, allowing the radioactivity to decay; short half-life elements were aged for 300 seconds or long half-life elements were aged for several days. After aging, the gamma-ray spectrum of the sample was recorded using a germanium semiconductor gamma-ray detector (ORTEC® model GEM55185, Advanced Measurement Technology Inc., Oak Ridge, Tenn., USA) and a multichannel analyzer (ORTEC model DSPEC Pro). The amount of each element in the sample was calculated from the gamma-ray spectrum and recorded in parts per million relative to the total weight of the ethylene polymer sample. The N.A.A. system was calibrated with Specpure standards (1000 ppm solutions of the desired element (greater than 99% pure)). One mL of solutions (elements of interest) were pipetted onto a 15 mm×800 mm rectangular paper filter and air dried. The filter paper was then placed in a 1.4 mL polyethylene irradiation vial and analyzed by the N.A.A. system. Standards are used to determine the sensitivity of the N.A.A. procedure (in counts/μg).

Examples 1-4 employ the unimodal polymers as described above. Comparative examples 6-9 are commercially available polymers having a melt index, $I_2$ ranging from about 1.5 to about 11.0 g/10 min and densities ranging from about 0.951 g/cm³ to about 0.955 g/cm³.

TABLE 4

NAA of Polyethylene Polymers

| Example | Al (Ppm) | Cl (ppm) | Mg (ppm) | Ti (ppm) |
|---|---|---|---|---|
| 1 | 0.96 | 0.14 | <2 | 0.19 |
| 2 | 0.58 | 0.1 | <2 | 0.69 |
| 3 | 0.511 | 0.074 | <1 | 0.288 |
| 4 | 0.19 | 0.11 | <1 | 0.16 |
| 6, Comp. | 66.3 | 20.2 | 3.61 | 7.27 |
| 7, Comp. | 65.2 | 32.6 | 4.05 | 12.19 |
| 8, Comp. | 25.1 | 9.54 | 2.89 | 0.923 |
| 9, Comp. | 26.2 | 11.3 | 3.97 | 1.01 |

The data provided in Table 4, shows that the resins employed in Examples 1-4 have much reduced residual catalyst component levels (e.g. aluminum, chlorine, magnesium and titanium) when compared to several other commercially available products (Examples 6 through 9). Compare for example, Examples 1-4 which have less than 1 ppm of aluminum (Al), and less than 0.7 ppm of titanium (Ti) present (where "ppm" is parts per million of element per mass of polymer, e.g., milligrams of element/kilograms of polymer) with Examples 6-9 which have Al levels of from about 25 ppm to about 66 ppm, and Ti levels of from about 1 to about 12 ppm. Examples 1-4 also have much lower levels of chlorine (Cl) and magnesium (Mg), which don't exceed about 0.15 ppm and 2 ppm, respectively.

For end use applications, especially those which may come in contact with foodstuff, it may be desirable to employ products having lower levels of catalyst component residues. Lower catalyst residues may lead to better organoleptic properties and help preserve the original taste and odor of the packaged contents.

Non-limiting embodiments of the present disclosure include the following:

Embodiment A

A hinged component comprising a polyethylene composition which is not a polymer blend and has a density of from 0.940 to 0.965 g/cm³, a melt index, $I_2$ of less than 30 g/10 min, a molecular weight distribution, $M_w/M_n$ of less than 5.0, and a unimodal profile in a GPC chromatograph.

Embodiment B

The hinged component of Embodiment A wherein the polyethylene composition has a melt flow ratio, $I_{21}/I_2$ of less than 40.

Embodiment C

The hinged component of Embodiment A or B wherein the polyethylene composition has a molecular weight distribution, $M_w/M_n$ of less than 3.5.

Embodiment D

The hinged component of Embodiment A, B or C wherein the polyethylene composition has a density of from 0.949 to 0.963 g/cm³.

Embodiment E

The hinged component of Embodiment A, B, C, or D wherein the polyethylene composition has a $M_z$ of less than 450,000.

Embodiment F

The hinged component of Embodiment A, B, C, D or E wherein the polyethylene composition has a $M_z/M_w$ of less than 3.0.

Embodiment G

The hinged component of Embodiment A, B, C, D, E or F wherein the polyethylene composition has a melt index, $I_2$ of less than 20 g/10 min.

Embodiment H

The hinged component of Embodiment A, B, C, D, E or F wherein the polyethylene composition has a melt index, $I_2$ of less than 10 g/10 min.

Embodiment I

The hinged component of Embodiment A, B, C, D, E or F wherein the polyethylene composition has a melt index, $I_2$ of from 2.5 to 9.5 g/10 min.

Embodiment J

The hinged component of Embodiment A, B, C, D, E or F wherein the polyethylene composition has a melt index, $I_2$ of at least 10 g/10 min.

Embodiment K

The hinged component of Embodiment A, B, C, D, E or F wherein the polyethylene composition has a melt index, $I_2$ of from 10.0 to 19.5 g/10 min.

Embodiment L

The hinged component of Embodiment A, B, C, D, E, F, G, H, I, J or K wherein the polyethylene composition has a melt flow ratio, $I_{21}/I_2$ of less than 30.

Embodiment M

The hinged component of Embodiment A, B, C, D, E, F, G, H, I, J, K or L wherein the polyethylene composition has an amount of terminal unsaturation of at least 0.45 per 1000 carbon atoms.

Embodiment N

The hinged component of Embodiment A, B, C, D, E, F, G, H, I, J, K, L or M wherein the polyethylene composition has a total amount of unsaturation of at least 0.50 per 1000 carbon atoms.

Embodiment O

The hinged component of Embodiment A, B, C, D, E, F, G, H, I, J, K, L, M or N wherein the polyethylene composition is a polyethylene copolymer of ethylene and one or more than one alpha-olefin.

Embodiment P

The hinged component of Embodiment A, B, C, D, E, F, G, H, I, J, K, L, M or N wherein the polyethylene composition is a polyethylene homopolymer.

Embodiment Q

The hinged component of Embodiment A, B, C, D, E, F, G, H, I, J, K, L, M or N wherein the polyethylene composition comprises polymerized ethylene and 1-butene.

Embodiment R

The hinged component of Embodiment A, B, C, D, E, F, G, H, I, J, K, L, M, N, O, P or Q wherein the polyethylene composition has fewer than 0.8 parts per million of titanium.

Embodiment S

The hinged component of Embodiment A, B, C, D, E, F, G, H, I, J, K, L, M, N, O, P, Q or R wherein the polyethylene composition is made in a solution phase polymerization reactor.

Embodiment T

The hinged component of Embodiment A, B, C, D, E, F, G, H, I, J, K, L, M, N, O, P, Q, R, or S wherein the polyethylene composition is made with a Ziegler-Natta catalyst.

Embodiment U

The hinged component of Embodiment A, B, C, D, E, F, G, H, I, J, K, L, M, N, O, P, Q, R, S or T wherein the hinged component has an average hinge life of at least 2,500 cycles.

Embodiment V

The hinged component of Embodiment A, B, C, D, E, F, G, H, I, J, K, L, M, N, O, P, Q, R, S, or T wherein the hinged component has an average hinge life of at least 3,500 cycles.

Embodiment W

The hinged component of Embodiment A, B, C, D, E, F, G, H, I, J, K, L, M, N, O, P, Q, R, S, T, U or V wherein the hinged component is injection molded.

Embodiment X

The hinged component of Embodiment A, B, C, D, E, F, G, H, I, J, K, L, M, N, O, P, Q, R, S, T, U, V, or W wherein the hinged component is a closure.

What is claimed is:

1. A hinged component comprising a polyethylene composition which is not a polymer blend and has a density of from 0.940 to 0.965 g/cm$^3$, a melt index, I2 of less than 30 g/10 min, a molecular weight distribution, $M_w/M_n$ of less than 5.0, and a unimodal profile in a GPC chromatograph; and wherein the polyethylene composition provides an average hinge life of from 2,400 to 4928 cycles in a hinge life test.

2. The hinged component of claim 1 wherein the polyethylene composition has a melt flow ratio, $I_{21}/I_2$ of less than 40.

3. The hinged component of claim 1 wherein the polyethylene composition has a molecular weight distribution, $M_w/M_n$ of less than 3.5.

4. The hinged component of claim 1 wherein the polyethylene composition has a density of from 0.949 to 0.963 g/cm$^3$.

5. The hinged component of claim 1 wherein the polyethylene composition has a $M_Z$ of less than 450,000.

6. The hinged component of claim 1 wherein the polyethylene composition has a $M_Z/M_W$ of less than 3.0.

7. The hinged component of claim 1 wherein the polyethylene composition has a melt index, $I_2$ of less than 20 g/10 min.

8. The hinged component of claim 1 wherein the polyethylene composition has a melt flow ratio, $I_{21}/I_2$ of less than 30.

9. The hinged component of claim 1 wherein the polyethylene composition has an amount of terminal unsaturation of at least 0.45 per 1000 carbon atoms.

10. The hinged component of claim 1 wherein the polyethylene composition has a total amount of unsaturation of at least 0.50 per 1,000 carbon atoms.

11. The hinged component of claim 1 wherein the polyethylene composition is a polyethylene copolymer of ethylene and one or more than one alpha-olefin.

12. The hinged component of claim 1 wherein the polyethylene composition is a polyethylene homopolymer.

13. The hinged component of claim 1 wherein the polyethylene composition has fewer than 0.8 parts per million of titanium.

14. The hinged component of claim 1 wherein the polyethylene composition comprises polymerized ethylene and 1-butene.

15. The hinged component of claim 1 wherein the hinged component is injection molded.

16. The hinged component of claim 1 wherein the polyethylene composition has a melt index, 12 of less than 10 g/10 min.

17. The hinged component of claim 1 wherein the polyethylene composition has a melt index, $I_2$ of from 2.5 to 9.5 g/10 min.

18. The hinged component of claim 1 wherein the polyethylene composition has a melt index, $I_2$ of at least 10 g/10 min.

19. The hinged component of claim 1 wherein the polyethylene composition has a melt index, $I_2$ of from 10.0 to 19.5 g/10 min.

20. The hinged component of claim 1 wherein the hinged component is a closure.

21. The hinged component of claim 16 wherein the hinged component is a closure.

22. The hinged component of claim 17 wherein the hinged component is a closure.

23. The hinged component of claim 18 wherein the hinged component is a closure.

24. The hinged component of claim 19 wherein the hinged component is a closure.

25. The hinged component of claim 1 wherein the polyethylene composition is made in a solution phase polymerization reactor.

26. The hinged component of claim 1 wherein the polyethylene composition is made with a Ziegler-Natta catalyst.

* * * * *